(12) United States Patent
Lee et al.

(10) Patent No.: US 9,220,646 B2
(45) Date of Patent: Dec. 29, 2015

(54) ABSORBENT ARTICLES WITH IMPROVED STAIN DECOLORIZATION

(71) Applicant: Kimberly-Clark Worldwide, Inc., Neenah, WI (US)

(72) Inventors: SangWook Lee, Seongnam-si (KR); Shruti Aryal, Beaverton, OH (US); Franz Aschenbrenner, Kastl (DE); JunMo Gil, DaeJeon (KR); Priscilla Eng Choo Goh, Singapore (SG); Kenneth G. Heckner, Combined Locks, WI (US); DooHong Kim, Seoul (KR); Ali Yahiaoui, Roswell, GA (US); Jun Zhang, Appleton, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 36 days.

(21) Appl. No.: 13/851,941

(22) Filed: Mar. 27, 2013

(65) Prior Publication Data
US 2013/0261586 A1 Oct. 3, 2013

Related U.S. Application Data

(60) Provisional application No. 61/618,172, filed on Mar. 30, 2012, provisional application No. 61/695,481, filed on Aug. 31, 2012.

(51) Int. Cl.
*A61F 13/15* (2006.01)
*A61F 13/84* (2006.01)
(Continued)

(52) U.S. Cl.
CPC ....... *A61F 13/8405* (2013.01); *A61F 13/47263* (2013.01); *A61F 13/513* (2013.01); *A61F 13/5116* (2013.01); *A61F 13/51113* (2013.01)

(58) Field of Classification Search
CPC ............ A61F 13/47263; A61F 13/8405; A61F 13/51113; A61F 13/5116; A61F 13/513; A61F 2013/530686; A61F 2013/530693; A61F 2013/8497
USPC .............. 604/359, 385.01, 367, 360, 362, 604/385.04, 361
See application file for complete search history.

(56) References Cited

U.S. PATENT DOCUMENTS

| 2,236,529 A | 4/1941 | Epstein et al. |
| 2,418,907 A | 4/1947 | Schreiber |

(Continued)

FOREIGN PATENT DOCUMENTS

| CN | 1034932 A | 8/1989 |
| CN | 1616115 A | 5/2005 |

(Continued)

OTHER PUBLICATIONS

Co-pending U.S. Appl. No. 13/851,927, filed Mar. 27, 2013, by Lee et al. for "Absorbent Articles with Decolorizing Agents."
(Continued)

*Primary Examiner* — Jacqueline Stephens
(74) *Attorney, Agent, or Firm* — Patrick C. Wilson

(57) ABSTRACT

Disclosed herein is a personal care absorbent article such as a feminine hygiene absorbent personal care article for receiving a body exudate such as menses. The article includes a topsheet layer, a backsheet layer, at least one absorbent core layer positioned between the topsheet layer and the backsheet layer, optionally a pair of wings, and a decolorization means associated with the article for altering the visual appearance and/or physical characteristics of the a body exudate. The use of the decolorization means provides several benefits to the end user including the creation of a visually smaller stain on the top surface of the topsheet layer and a possible reduction in staining of the wearer's apparel should the body exudate leak from or off of the article being worn.

16 Claims, 11 Drawing Sheets

(51) Int. Cl.
 A61F 13/513 (2006.01)
 A61F 13/472 (2006.01)
 A61F 13/511 (2006.01)

(56) References Cited

U.S. PATENT DOCUMENTS

| | | |
|---|---|---|
| 2,542,909 A | 2/1951 | De Wet et al. |
| 3,124,135 A | 3/1964 | Olson |
| 3,287,222 A | 11/1966 | Raymond et al. |
| 3,338,992 A | 8/1967 | Kinney |
| 3,341,394 A | 9/1967 | Kinney |
| 3,347,236 A | 10/1967 | David |
| 3,397,697 A | 8/1968 | Rickard |
| 3,398,097 A | 8/1968 | Kersnar et al. |
| 3,490,454 A | 1/1970 | Goldfarb et al. |
| 3,502,538 A | 3/1970 | Petersen |
| 3,502,763 A | 3/1970 | Hartmann |
| 3,542,615 A | 11/1970 | Dobo et al. |
| 3,635,828 A | 1/1972 | Benjamin et al. |
| 3,663,445 A | 5/1972 | Augustin et al. |
| 3,692,618 A | 9/1972 | Dorschner et al. |
| 3,783,872 A | 1/1974 | King |
| 3,802,817 A | 4/1974 | Matsuki et al. |
| 3,814,101 A | 6/1974 | Kozak |
| 3,849,241 A | 11/1974 | Butin et al. |
| 3,953,351 A | 4/1976 | Keller |
| 3,979,318 A | 9/1976 | Tokiwa et al. |
| 4,100,324 A | 7/1978 | Anderson et al. |
| 4,190,563 A | 2/1980 | Bosley et al. |
| 4,250,257 A | 2/1981 | Lee et al. |
| 4,259,383 A | 3/1981 | Eggensperger et al. |
| 4,288,225 A | 9/1981 | Roland et al. |
| 4,340,563 A | 7/1982 | Appel et al. |
| 4,357,939 A | 11/1982 | Roeder et al. |
| 4,363,322 A | 12/1982 | Andersson |
| 4,381,784 A | 5/1983 | Aberson et al. |
| 4,431,560 A | 2/1984 | Lake et al. |
| 4,532,232 A | 7/1985 | Larsson et al. |
| 4,585,650 A | 4/1986 | Newberry, Jr. et al. |
| 4,594,327 A | 6/1986 | Zuk |
| 4,636,209 A | 1/1987 | Lassen |
| 4,655,759 A | 4/1987 | Romans-Hess et al. |
| 4,673,524 A | 6/1987 | Dean |
| 4,693,713 A | 9/1987 | Chmelir et al. |
| 4,773,423 A | 9/1988 | Hakky |
| 4,798,603 A | 1/1989 | Meyer et al. |
| 4,801,494 A | 1/1989 | Datta et al. |
| 4,803,153 A | 2/1989 | Shibata et al. |
| 4,847,089 A | 7/1989 | Kramer et al. |
| 4,855,108 A | 8/1989 | Masuda et al. |
| 4,886,512 A | 12/1989 | Damico et al. |
| 4,892,534 A | 1/1990 | Datta et al. |
| 4,908,026 A | 3/1990 | Becker et al. |
| 4,933,092 A | 6/1990 | Aunet et al. |
| 5,009,716 A | 4/1991 | Gerson |
| 5,037,412 A | 8/1991 | Tanzer et al. |
| 5,064,541 A | 11/1991 | Jeng et al. |
| 5,118,428 A | 6/1992 | Sand et al. |
| 5,147,698 A | 9/1992 | Cole |
| 5,223,284 A | 6/1993 | Kulczycki, Jr. et al. |
| 5,248,309 A * | 9/1993 | Serbiak et al. ............ 604/368 |
| 5,262,153 A | 11/1993 | Mishima et al. |
| 5,281,208 A | 1/1994 | Thompson et al. |
| 5,284,703 A | 2/1994 | Everhart et al. |
| 5,340,493 A | 8/1994 | Principato |
| 5,340,495 A | 8/1994 | Mulcahy et al. |
| 5,350,624 A | 9/1994 | Georger et al. |
| 5,382,400 A | 1/1995 | Pike et al. |
| 5,389,282 A | 2/1995 | Saijo et al. |
| 5,401,267 A | 3/1995 | Couture-Dorschner et al. |
| 5,407,442 A | 4/1995 | Karapasha |
| 5,415,640 A | 5/1995 | Kirby et al. |
| 5,434,059 A | 7/1995 | Balaraman et al. |
| 5,447,689 A | 9/1995 | Gibboni et al. |
| 5,505,720 A | 4/1996 | Hujber et al. |
| 5,527,892 A | 6/1996 | Borsotti et al. |
| 5,558,659 A | 9/1996 | Sherrod et al. |
| 5,558,834 A | 9/1996 | Chu et al. |
| 5,575,785 A | 11/1996 | Gryskiewicz et al. |
| 5,595,754 A | 1/1997 | Ito et al. |
| 5,607,414 A | 3/1997 | Richards et al. |
| 5,607,760 A | 3/1997 | Roe |
| 5,614,295 A | 3/1997 | Quincy, III et al. |
| 5,649,916 A | 7/1997 | Dipalma et al. |
| 5,652,148 A | 7/1997 | Doshi et al. |
| 5,660,798 A | 8/1997 | Doshi et al. |
| 5,695,679 A | 12/1997 | Christie et al. |
| 5,755,710 A | 5/1998 | Menard |
| 5,762,642 A | 6/1998 | Coles et al. |
| 5,766,552 A | 6/1998 | Doshi et al. |
| 5,770,543 A | 6/1998 | Garst et al. |
| 5,785,696 A | 7/1998 | Inoue et al. |
| 5,795,344 A | 8/1998 | Chappell |
| 5,807,361 A | 9/1998 | Kajikawa et al. |
| 5,810,798 A | 9/1998 | Finch et al. |
| 5,883,231 A | 3/1999 | Achter et al. |
| 5,899,893 A | 5/1999 | Dyer et al. |
| 5,912,194 A | 6/1999 | Everhart et al. |
| 5,961,505 A | 10/1999 | Coe et al. |
| 6,110,158 A | 8/2000 | Kielpikowski |
| 6,117,523 A | 9/2000 | Sugahara |
| 6,168,654 B1 | 1/2001 | Nohr et al. |
| 6,171,682 B1 | 1/2001 | Raidel et al. |
| 6,172,276 B1 | 1/2001 | Hetzler et al. |
| 6,231,719 B1 | 5/2001 | Garvey et al. |
| 6,241,714 B1 | 6/2001 | Raidel et al. |
| 6,322,544 B1 | 11/2001 | Laughlin et al. |
| 6,348,253 B1 | 2/2002 | Daley et al. |
| 6,350,711 B1 | 2/2002 | Potts et al. |
| 6,369,293 B1 | 4/2002 | Reeves et al. |
| 6,436,080 B1 | 8/2002 | Carlucci et al. |
| 6,471,728 B2 | 10/2002 | Smith et al. |
| 6,511,465 B1 | 1/2003 | Freiburger et al. |
| 6,528,698 B2 | 3/2003 | Mizutani et al. |
| 6,534,149 B1 | 3/2003 | Daley et al. |
| 6,548,731 B2 | 4/2003 | Mizutani et al. |
| 6,559,353 B1 | 5/2003 | Sheridan |
| 6,580,015 B2 | 6/2003 | Reeves et al. |
| 6,586,653 B2 | 7/2003 | Graeme, III et al. |
| 6,613,028 B1 | 9/2003 | Daley et al. |
| 6,642,430 B1 | 11/2003 | Busam et al. |
| 6,663,611 B2 | 12/2003 | Blaney et al. |
| 6,667,424 B1 | 12/2003 | Hamilton et al. |
| 6,669,932 B2 | 12/2003 | Imanaka et al. |
| 6,673,374 B2 | 1/2004 | Murad |
| 6,673,982 B1 | 1/2004 | Chen et al. |
| 6,677,498 B2 | 1/2004 | Chen et al. |
| 6,696,240 B1 | 2/2004 | Kloepfer et al. |
| 6,703,538 B2 | 3/2004 | Lassen et al. |
| 6,730,819 B1 | 5/2004 | Pesce |
| 6,812,169 B2 | 11/2004 | Potts et al. |
| 6,838,423 B2 | 1/2005 | Irvin et al. |
| 6,867,344 B2 | 3/2005 | Potts et al. |
| 6,875,617 B2 | 4/2005 | Alam |
| 6,888,044 B2 | 5/2005 | Fell et al. |
| 6,896,669 B2 | 5/2005 | Krautkramer et al. |
| 6,929,629 B2 | 8/2005 | Drevik et al. |
| 6,932,929 B2 | 8/2005 | Krautkramer et al. |
| 6,974,891 B2 | 12/2005 | Wallstroem |
| 6,984,770 B2 | 1/2006 | Graeme, III et al. |
| 7,105,715 B2 | 9/2006 | Carlucci et al. |
| 7,160,278 B2 | 1/2007 | Mizutani et al. |
| 7,241,627 B2 | 7/2007 | Wilhelm et al. |
| D558,335 S | 12/2007 | Willhaus |
| 7,316,673 B2 | 1/2008 | Drevik et al. |
| 7,388,123 B2 | 6/2008 | Cowell et al. |
| 7,402,157 B2 | 7/2008 | Christon et al. |
| 7,429,689 B2 | 9/2008 | Chen et al. |
| 7,431,715 B2 | 10/2008 | Guidotti et al. |
| 7,431,775 B2 | 10/2008 | Wang et al. |
| 7,504,551 B2 | 3/2009 | Herfert et al. |
| 7,687,681 B2 | 3/2010 | Di Luccio et al. |
| 7,695,726 B2 | 4/2010 | Rosevear et al. |
| 7,722,906 B2 | 5/2010 | Kandil |

(56) References Cited

U.S. PATENT DOCUMENTS

| | | | |
|---|---|---|---|
| 7,723,093 B2 | 5/2010 | Kwon et al. |
| 7,837,944 B2 | 11/2010 | Auner et al. |
| 7,846,281 B2 | 12/2010 | Muvundamina |
| 7,879,744 B2 | 2/2011 | Seidling et al. |
| 7,928,282 B2 | 4/2011 | Dibb et al. |
| 8,003,780 B2 | 8/2011 | Kim et al. |
| 8,029,487 B2 | 10/2011 | Bagger-Sjoebaeck et al. |
| 8,148,598 B2 | 4/2012 | Tsang et al. |
| 8,211,078 B2 | 7/2012 | Noel |
| 8,241,915 B2 | 8/2012 | Adamczyk et al. |
| 8,283,515 B2 | 10/2012 | Lagerstedt-Eidrup et al. |
| 8,367,013 B2 | 2/2013 | Kaylor et al. |
| 8,461,411 B2 | 6/2013 | Digiacomantonio et al. |
| 8,461,412 B2 | 6/2013 | Febo et al. |
| 8,569,221 B2 | 10/2013 | Cunningham et al. |
| 8,847,002 B2 | 9/2014 | Goh et al. |
| 2002/0022813 A1 | 2/2002 | Bewick-Sonntag et al. |
| 2002/0040210 A1* | 4/2002 | Luccio et al. ........ 604/367 |
| 2002/0054918 A1 | 5/2002 | Murad |
| 2002/0082571 A1 | 6/2002 | Krivan et al. |
| 2002/0120242 A1 | 8/2002 | Tyrrell et al. |
| 2003/0100877 A1 | 5/2003 | Erdman |
| 2003/0103916 A1 | 6/2003 | Imanaka et al. |
| 2003/0109839 A1 | 6/2003 | Costea et al. |
| 2003/0114811 A1 | 6/2003 | Christon et al. |
| 2003/0114818 A1 | 6/2003 | Benecke et al. |
| 2003/0119202 A1 | 6/2003 | Kaylor et al. |
| 2003/0124336 A1 | 7/2003 | Keane et al. |
| 2003/0130631 A1 | 7/2003 | Springer et al. |
| 2003/0162681 A1 | 8/2003 | Hage et al. |
| 2003/0204178 A1 | 10/2003 | Febo et al. |
| 2003/0208173 A1 | 11/2003 | Lagerstedt-Eidrup et al. |
| 2004/0015145 A1 | 1/2004 | Miura et al. |
| 2004/0022678 A1 | 2/2004 | Komagoe et al. |
| 2004/0060112 A1 | 4/2004 | Fell et al. |
| 2004/0064119 A1 | 4/2004 | Guidotti et al. |
| 2004/0127883 A1 | 7/2004 | Cowell et al. |
| 2005/0079637 A1 | 4/2005 | Wilhelm et al. |
| 2005/0148488 A1 | 7/2005 | Jekel et al. |
| 2005/0163730 A1 | 7/2005 | Rosevear et al. |
| 2005/0214241 A1 | 9/2005 | Kandil |
| 2005/0256022 A1 | 11/2005 | May et al. |
| 2006/0111266 A1 | 5/2006 | Abera et al. |
| 2006/0127437 A1 | 6/2006 | Kennedy et al. |
| 2006/0189817 A1 | 8/2006 | Horlacher et al. |
| 2006/0198797 A1 | 9/2006 | Giniger |
| 2006/0222675 A1 | 10/2006 | Sabnis et al. |
| 2007/0027049 A1 | 2/2007 | Rigg |
| 2007/0055210 A1 | 3/2007 | Kao |
| 2007/0087954 A1 | 4/2007 | Wang et al. |
| 2007/0093770 A1 | 4/2007 | Ecker et al. |
| 2007/0116748 A1 | 5/2007 | Isele et al. |
| 2007/0122360 A1 | 5/2007 | Oniki et al. |
| 2007/0197987 A1 | 8/2007 | Tsang et al. |
| 2008/0276379 A1 | 11/2008 | MacDonald et al. |
| 2008/0277621 A1 | 11/2008 | MacDonald et al. |
| 2008/0299609 A1 | 12/2008 | Kwon et al. |
| 2009/0036856 A1 | 2/2009 | Woltman et al. |
| 2009/0047363 A1 | 2/2009 | Itoi et al. |
| 2009/0061718 A1 | 3/2009 | Seidling et al. |
| 2009/0062172 A1 | 3/2009 | Cunningham et al. |
| 2009/0062764 A1 | 3/2009 | MacDonald et al. |
| 2009/0105676 A1 | 4/2009 | Brusk et al. |
| 2009/0156536 A1 | 6/2009 | Kim et al. |
| 2009/0157021 A1 | 6/2009 | Sullivan et al. |
| 2009/0238847 A1 | 9/2009 | Itoi et al. |
| 2009/0280553 A1 | 11/2009 | Mikami et al. |
| 2009/0306615 A1 | 12/2009 | Olsson |
| 2010/0028638 A1 | 2/2010 | Reichardt et al. |
| 2011/0004174 A1 | 1/2011 | Carlucci et al. |
| 2011/0251575 A1 | 10/2011 | Kuroda et al. |
| 2011/0288514 A1 | 11/2011 | Kuroda et al. |
| 2012/0109088 A1 | 5/2012 | Komatsu et al. |
| 2012/0115718 A1 | 5/2012 | Nakashita et al. |
| 2012/0141975 A1 | 6/2012 | Sato et al. |
| 2012/0165773 A1 | 6/2012 | Nakashita et al. |
| 2012/0215192 A1 | 8/2012 | Corbellini et al. |
| 2012/0296303 A1 | 11/2012 | Ng et al. |
| 2013/0012900 A1 | 1/2013 | Uda et al. |
| 2013/0158494 A1 | 6/2013 | Ong et al. |
| 2013/0261584 A1 | 10/2013 | Lee et al. |
| 2013/0261585 A1 | 10/2013 | Lee |
| 2013/0261586 A1 | 10/2013 | Lee et al. |

FOREIGN PATENT DOCUMENTS

| | | |
|---|---|---|
| CN | 200948202 Y | 9/2007 |
| DE | 10 2009 029 194 A1 | 4/2011 |
| EP | 0 019 371 A1 | 11/1980 |
| EP | 0 355 842 A2 | 2/1990 |
| EP | 0 470 275 A1 | 2/1992 |
| EP | 0 560 630 B1 | 11/1998 |
| EP | 1 034 799 A1 | 9/2000 |
| EP | 1 034 801 A1 | 9/2000 |
| EP | 1 034 803 A1 | 9/2000 |
| EP | 1 034 804 A1 | 9/2000 |
| EP | 1 358 894 A1 | 11/2003 |
| EP | 1 295 711 B1 | 4/2006 |
| EP | 1 356 797 B1 | 12/2006 |
| EP | 1 159 014 B1 | 4/2007 |
| EP | 1 842 513 A1 | 10/2007 |
| EP | 2 269 661 B1 | 11/2012 |
| GB | 792531 A | 3/1958 |
| GB | 1 349 955 A | 4/1974 |
| GB | 2 090 137 A | 7/1982 |
| GB | 2 390 853 A | 1/2004 |
| JP | 63-134050 A | 6/1988 |
| JP | 01-186809 A | 7/1989 |
| JP | 01-213231 A | 8/1989 |
| JP | 03-172400 A | 7/1991 |
| JP | 03-215267 A | 9/1991 |
| JP | 7028890 B4 | 4/1995 |
| JP | 2001-070339 A | 3/2001 |
| JP | 4184253 B2 | 11/2008 |
| KR | 10-2009-0100645 A | 9/2009 |
| WO | WO 97/46219 A1 | 12/1997 |
| WO | WO 98/10928 A1 | 3/1998 |
| WO | WO 99/26588 A2 | 6/1999 |
| WO | WO 00/37039 A1 | 6/2000 |
| WO | WO 00/51655 A1 | 9/2000 |
| WO | WO 00/51656 A1 | 9/2000 |
| WO | WO 01/12241 A1 | 2/2001 |
| WO | WO 01/16268 A1 | 3/2001 |
| WO | WO 03/041752 A1 | 5/2003 |
| WO | WO 03/052390 A1 | 6/2003 |
| WO | WO 2005/107670 A2 | 11/2005 |
| WO | WO 2006/062679 A2 | 6/2006 |
| WO | WO 2006/117055 A1 | 11/2006 |
| WO | WO 2007/085626 A1 | 8/2007 |
| WO | WO 2008/139340 A1 | 11/2008 |
| WO | WO 2008/139341 A2 | 11/2008 |
| WO | WO 2009/027856 A2 | 3/2009 |
| WO | WO 2009/062998 A1 | 5/2009 |
| WO | WO 2009/133518 A2 | 11/2009 |
| WO | WO 2010/017158 A1 | 2/2010 |
| WO | WO 2011/027295 A2 | 3/2011 |
| WO | WO 2012/074512 A1 | 6/2012 |

OTHER PUBLICATIONS

Co-pending U.S. Appl. No. 13/851,932, filed Mar. 27, 2013, by Lee for "Absorbent Articles with Decolorizing Structures."

American Society for Testing Materials (ASTM) Designation: E1164-02, "Standard Practice for Obtaining Spectrometric Data for Object-Color Evaluation," pp. 1-8, published Aug. 2002.

Cost, Frank, "Pocket Guide to Digital Printing," Delmar Publishers, Albany, NY, ISBN 0-8273-7592-1, pp. 144-145, Jul. 31, 1996.

Field Guide to Stains—How to Identify and Remove Virtually Every Stain Known to Man, Quirk Productions, Inc., 2002, pp. 199-202, Sep. 1, 2002.

Japanese Industrial Standard, JIS Z 8722:2000, "Methods of Colour Measurement—Reflecting and Transmitting Objects," 2000, 1-57 and 1 correction page, "Errata,", May 20, 2000.

(56) References Cited

OTHER PUBLICATIONS

Lindon, Jack et al., "A Biological Menses Simulant Using a "Batch" Homogenization Process With Varying Levels of Rheological Properties," ip.com, IPCOM000198395D, Aug. 6, 2010, pp. 1-13.
Fatty acid. Wikipedia, Internet web page "http://en.wikipedia.org/wiki/Fatty_acid", viewed and printed Jul. 25, 2013, pp. 1-14.
Oxidizing agent. Wikipedia, Internet web page "http://en.wikipedia.org/wiki/Oxidizer", viewed and printed Jul. 25, 2013, pp. 1-6.
On-the-spot cleanup, Consumer Reports, Jun. 1998, p. 10.
Seeing Spots? Don't Rely on Quick Stain Removers, Consumer Reports, Aug. 2006, p. 9.
Stain Removers: Which Are Best?, Consumer Reports, Mar. 2000, p. 52.
Cacace, M.G. et al., "The Hofmeister Series: Salt and Solvent Effects on Interfacial Phenomena," Quarterly Reviews of Biophysics, vol. 30, No. 3, 1997, pp. 241-277, Aug. 1997.
Senczuk, Anna M. et al., "Hydrophobic Interaction Chromatography in Dual Salt System Increases Protein Binding Capacity," Biotechnology and Bioengineering, vol. 103, No. 5, Aug. 1, 2009, pp. 930-935.

* cited by examiner

ABSORBENT ARTICLES WITH IMPROVED STAIN DECOLORIZATION

This application claims the benefit of priority from U.S. Provisional Application No. 61/618,172 filed on Mar. 30, 2012 and from U.S. Provisional Application No. 61/695,481 filed on Aug. 31, 2012, the subject matter of each of which is hereby incorporated by reference herein.

FIELD OF THE INVENTION

The present invention is generally directed to absorbent personal care articles. In particular, the present invention is directed to feminine hygiene absorbent personal care articles having portions which come in contact with exudates including menses, and which portions can be used to chemically alter or physically separate such exudates to change the visual perception of the functioning of the product and the staining potential associated with the use of such products.

BACKGROUND OF THE INVENTION

Personal care absorbent articles include such products as diapers, diaper pants, training pants, feminine hygiene products, adult incontinence products, bandages and the like. Such products are designed to absorb and contain a wide variety of body exudates including blood, urine menses, feces and other body fluids.

Feminine hygiene absorbent personal care articles are often used to collect and retain body fluids, liquids or exudates containing menses or blood. In the context of such products, comfort, absorbency, and discretion are three main product attributes and areas of concern for the wearer. In particular, wearers are often interested in knowing that such products will absorb significant volumes of menses exudates in order to protect their undergarments, outergarments, or bedsheets from staining, and that such products will help them avoid the subsequent embarrassment brought on by such staining. Wearers are also interested in using products that cannot be seen or felt through their undergarments.

Feminine hygiene absorbent personal care articles, such as sanitary napkins, pads and pantiliners, typically include at least one or more absorbent layers enclosed between a body-facing, liquid permeable topsheet layer and a garment-facing liquid impermeable backsheet layer with the peripheral edges of the topsheet and backsheet being bonded to one another to form a seal around the article to thereby contain the absorbent layers and any exudates received into the article through the topsheet. In use, such articles are typically positioned in the crotch portion of an undergarment for absorption of bodily exudates, and are held in place via adhesive strips positioned on the undersurface of the articles (facing the garment). Some of these articles also include wing-like structures for wrapping about the user's undergarments to further secure them to a user's underwear. Such wing-like structures are frequently made from lateral extensions of the topsheet and backsheet layers.

For many women, it is entirely routine to periodically view their hygienic articles during use so as to monitor the appearance and spread of a menses insult (so as to avoid leakage throughout the day). For some women, a concern or cause of emotional discomfort with conventional feminine hygiene absorbent personal care articles is the visually expanding size and appearance of a menses insult in the article, and specifically, the spread of the menses stain to the side edges of a product. While many women often do not mind seeing a targeted staining in the center of a pad, and then change the pad accordingly, some women prefer not to see an extensive stain, other than the centralized insult stain. In contrast, some women prefer to see an expanding stain, as this provides indication of their level of flow that day, as well as evidence that the pad is collecting such exudates. Obviously, the leakage of fluids when using such articles, particularly from around the side and end edges of the articles, is universally a cause of emotional concern. Such leakage may occur in the narrower product dimension along the longitudinally directed side edges, or along the wing or flap areas. Product leakage may lead not only to embarrassment for the consumer, but also to a general loss of confidence in use of the articles.

Various attempts have therefore been made to incorporate chemistry or structures into feminine hygienic pads to separate staining, direct staining, target staining, mask staining or discolor menses staining; to make more efficient use of as much of an absorbent product as possible; and to reduce or prevent leakage. Such structures include embossed walls or channels, printed target areas, polymeric or other liquid impermeable barrier walls, and the like. However, such attempts have not been completely successful at eliminating or addressing the leakage problem, or reducing consumer concerns over staining, if it actually were to occur.

Attempts have also been made to chemically alter and separate components of menses along the depth direction of a pad, and thus reduce the mental impact of a possible stain, should menses strike through an absorbent layer to the bottom of a sanitary napkin. For example, U.S. Pat. No. 3,124,135 to Olson discloses the use of salts on a pad's interior layers (sandwiched between absorbent core layers and having the same lateral dimensions of the absorbent layers), so as to decolorize menses by precipitating the darker colored hemoglobin of the menses, as fluid travels in the depth direction of the pad. Such decolorization allows almost clear menses liquid to flow to various portions of lower absorbent layers and away from the precipitated hemoglobin. Such decolorization also allows clear menses liquid to potentially flow through a lower absorbent layer to the bottom of a pad, thereby reducing the occurrence of a visible stain at the bottom of a pad. The Olson reference highlights the stiffness produced in a pad as a result of the interior salt-containing layers, and offers a pad softening-solution, by use of polyethylene glycol (hereinafter PEG) as an additional filler with the impregnated salt elements on the interior layers of a pad. However, even with such salt and PEG combinations, the placement of this agglomeration chemistry on, or immediately near the absorbent layers, and having the same dimensions as the absorbent layers in the depth direction, can lead to the blocking of absorbency pathways in an article. Possible leakage may then result from the redirected fluid. The Olson reference does not address staining that results from pad leakage off of the pad top surface, either as a result of fluid flow or saturation of a subjacent absorbent layer. Nor does the Olson reference address the concern of consumers that would rather limit their viewing of a stain in a pad, when viewing a pad from the top surface. There is therefore still a need to lessen leakage, and to alter the stain-producing fluid off of a pad top surface, so as to lessen the mental impact of a menses insult (and potential leakage stain) for pad users, without interfering with the functioning of a product's absorbent layers; there is also a need for such alteration of the stain-producing fluid without impacting product "feel"; and there is also a need for a pad which limits staining potential as well a consumer's view of a stain within the pad.

Numerous absorbent structures have also been developed for capturing and retaining voluminous menses exudates released by women during their monthly cycles. In this regard, the designs of such absorbent pads and pantiliners have been refined over time, so as to make their usage more comfortable (physically and emotionally) to consumers. For example, originally when first developed, catamenial pads were thick and bulky structures, typically using cellulosic wadding as their sole or primary absorbent layer, such as described in U.S. Pat. No. 3,124,135 to Olson. Such pads were often readily visible through a wearer's outer garments, were used in conjunction with separate belts or tabs, and proved uncomfortable for a user to wear. These older "tabbed" or belted pads distributed menses predominately in the depth direction of the pad, and predominately leaked through the back of the pad. This fluid distribution was driven by a close to the body fit, due to the pad being used in combination with a belt construction. These pads were typically over ¾ inch (9 millimeters) thick, and employed no impervious layers to impede menses or air movement through the pad, and offered no specific distribution materials to drive lateral or longitudinal fluid distribution. These older pads needed constructions that prevented downward distribution of the red stain of menses. These pads also did not contain any superabsorbent that might interfere with the distribution of menses within the pad. As a result, such older constructions would not work adequately on modern, garment-attached pad arrangements.

As absorbent technology advanced, superabsorbent polymer chemistry and substrate layering designs have been developed, enabling manufacturers to produce feminine absorbent products with progressively thinner configurations. As a result, feminine hygiene sanitary napkins, pads and liners have become significantly thinner and more absorbent, so as to impart both comfort and a certain inconspicuousness to a wearer. For the most part, such thinner products have provided the users and surrounding third parties, with the impression that the user is not wearing any form of menses protection in her undergarments. Such articles have employed garment attachment systems.

The modern garment-attached pads predominately distribute menses laterally and longitudinally, and predominately leak off the side edges (longitudinally directed sides, front, and back) rather than through the pad bottom. This leakage distribution is driven by not-so-close pad body fit, due to attachment to underwear or panties, and the pad construction. These pads are typically less than ¼ inch (6.4 millimeters) thick, have an impervious layer to impede menses and air movement through the pad, and utilize specific distribution materials to drive lateral and longitudinal distribution. Modern pads also contain superabsorbent that can interfere with the distribution of menses within the pad. The use of superabsorbent materials in core layers can lead to gel blocking that interferes with maximized fluid absorption.

Even with these advancements in absorbency, consumers continue to experience some leakage, typically from fluid run-off from the topsheet surface. Such run-off is often the result of various "structural" and "action-based" root causes, which cause soiling of user garments or bedding. For example, structural causes may include impeded absorbency pathways, or inability to handle fluid surges. Action-based causes may be for example, consumers experiencing leakage from improper placement of such products in their undergarments, a consumer's use of such products beyond the product's designed lifespan, consumers choosing to wear an absorbent article that is ill equipped to handle their current menses flow rate, or further still, consumer movements during their daily activities which cause menses exudates to leak off of the absorbent article. Therefore, despite the development of many different absorbent technologies and structural designs, product leakage and the resulting stains caused from such leakage continue to concern potential users of such products. Mere adaptation of older decolorization technology to modern pad structures would not be adequate, as it does not account for interference from modern superabsorbents (superabsorbent competes with the decolorization technology for the menses), lack of adequate surface area, and modern day pad menses distribution, to prevent locally overwhelming the decolorization technology. A need therefore exists for pad constructions that prevent lateral and longitudinal distribution of the red stain of menses.

Trends in modern day feminine hygiene products are to make the products as thin and narrow as possible which results in a much smaller target zone for deposited fluids. Modern designs also dictate that the overall size of the products be made smaller which also can exacerbate fluid handling problems. This is especially true when the products are subjected to rapid and excessive flows of menstrual fluid, also referred to as "gushes." In such situations, today's products need to be more effective at absorbing fluids and minimizing the size of the deposited stains on the top surfaces of such products because as the deposited fluids move closer to the edges of the products, the risk of leaks and spills increases. Thus, a further need exists for a pad construction where, if a spill or leak of menses does occur, the typical red or dark color of the menses will be reduced in the leaking fluid so as to reduce the visibility of the staining menses material thereby lessening the potential for embarrassing displays of the leaked fluid. Still a further need exists for pad constructions which, while still being able to absorb large amounts of body exudates, such as menses, will give the perception that the stain size on the top surface is still relatively small as compared to the overall amount of exudate actually absorbed by the product.

Certain sensors or condition change indicators are known for use with feminine hygiene absorbent articles and other types of absorbent articles, to notify a user or caregiver of the impending need to change such article as a result of a change in condition. Such devices may assist in providing consumers with calmed emotional states, knowing that the devices are actively communicating impending product failure or body states. Such indicators can be seen for example in US 20030130631 to Springer and US 20070055210 to Kao. While, such devices are focused primarily on preventing leakage or staining, or the onset of some other condition by limiting user wear time, such devices do not assist in altering potential staining, should leakage actually occur. There is therefore a further need for such products which would reduce consumer emotional concerns of such staining, and the embarrassment that might accompany such staining.

As previously described, certain chemistry for the decolorization of blood stains on absorbent articles is known. For example, colorant changers, neutralizers or decolorizing compositions are described in U.S. 20080277621 to MacDonald, U.S. 20090061718 to Seidling, U.S. 20090062764 to MacDonald, WO02009133518 to Cunningham, U.S. Pat. No. 6,730,819 to Pesce, U.S. Pat. No. 7,105,715 to Carlucci, U.S. Pat. No. 3,124,135 to Olson, U.S. 20110004174 to Carlucci, and WO2011027295 to Corbellini, each of which are hereby incorporated by reference in their entirety. Also see U.S. Pat. No. 4,381,784 to Aberson et al. and U.S. Pat. No. 6,350,711 to Potts et al. as well as U.S. Patent Publication Nos. 2003/0114818 to Benecke et al.; 2012/0165773 to Nakashita et al.; and 2012/0215192 to Corbellini et al. Such chemistries are often difficult to place uniformly on a product surface, or to manipulate into a high enough surface area. Further, such chemistries may often result in a heavier, stiffer, and a subsequently more uncomfortable feeling article. Finally, such chemistries may result in menses color alterations that are less desirable to a consumer. Therefore, even with these available chemistries for decolorization, there is a further need for absorbent structures which utilize both layering structures and chemistry, to reduce the severity/appearance of menses staining of both a user's pad, and a user's garments or bedding. There is also a need for absorbent articles which reduce a consumer's concern over any stain that might occur, as well as articles which more efficiently use absorbent systems to take up retained liquids.

SUMMARY OF THE INVENTION

In one embodiment a personal care absorbent article such as a feminine hygiene absorbent personal care article for receiving a body exudate is disclosed which includes a topsheet layer, a backsheet layer, and at least one absorbent core layer having a peripheral edge positioned between the topsheet layer and the backsheet layer. The article defines a longitudinal axis, a transverse axis and a vertical or depth axis with the topsheet layer having a user facing surface having a first region for receiving the body exudate. The user facing surface also includes a second region capable of receiving the body exudate from the first region and a decolorization means located, at least in part, outboard of the peripheral edge of the absorbent core for altering the visual appearance of the body exudate in the second region as compared to the first region. The first region is devoid of the decolorization means. If desired, the decolorization means may comprise two separate means spaced laterally apart from one another.

If the body exudate is menses, which includes blood cells, the first region will be of a darker color than the second region due to the first region having a higher content of red blood cells than the second region. As a result of the use of decolorization means, the exudate in the second region will be less likely to stain a wearer's clothing than the exudate from the first region.

In some embodiments, the second region of the article can completely surround the first region. In other embodiments, the second region can be positioned laterally outboard of the first region. In still further embodiments, the article can have opposed longitudinal end portions and the second region can be located in the opposed longitudinal end portions of the article.

The personal care absorbent article can have opposed lateral side portions and the second region can be located in the opposed lateral side portions of the article. Alternately, the personal care absorbent article can have decolorization means associated with the user facing surface of the topsheet layer between the first region and the second region. By associated it is meant that the decolorization means can be attached to the user facing surface, it can be incorporated into the user facing surface of the topsheet layer or it can be located on the underside of the topsheet layer.

When the decolorization means is associated with the user facing surface, it can completely surround the first region or it can be located laterally outboard of the first region. As a result, if the body exudate comprises menses which contains red blood cells, the second region will have a lower concentration of the red blood cells than the first region. Additionally, the decolorization means can have a higher concentration of the red blood cells than the second region and the decolorization means can also have a higher concentration of red blood cells than either the first region or the second region.

In any of the embodiments of a personal care absorbent article disclosed herein, the article can further include wings associated with the article which are adapted to wrap around the crotch region of a wearer's underwear with the second region extending into the wings.

In another embodiment, a personal care absorbent article for receiving a body exudate is disclosed which includes a topsheet layer, a backsheet layer, and at least one absorbent core layer having a peripheral edge positioned between the topsheet layer and the backsheet layer with the article defining a longitudinal axis, a transverse axis and a vertical axis. The topsheet layer can have a user facing surface having a first region for receiving the body exudate. The user facing surface also has a second region capable of receiving body exudate from the first region. A decolorization means is located outboard of the peripheral edge of the absorbent core for altering the visual appearance of the body exudate in the second region as compared to the first region. The body exudate in the first region creates a first stain region with a lateral dimension and a longitudinal dimension that defines a first size and the article has a second stain region located below the first stain region relative to the vertical axis with the second stain region having a lateral dimension and a longitudinal dimension that defines a second size with the second size being larger than the first size.

In yet another embodiment, a personal care absorbent article for receiving a body exudate is disclosed which includes a topsheet layer, a backsheet layer, and at least one absorbent core layer having a peripheral edge positioned between the topsheet layer and the backsheet layer. The article defines a longitudinal axis, a transverse axis and a vertical axis with the topsheet layer having a user facing surface having a first region for receiving body exudate. The user facing surface also includes a second region capable of receiving body exudate from the first region with a decolorization means located outboard of the peripheral edge of the absorbent core for altering the physical characteristics of the body exudate in the second region as compared to the first region.

Objects and advantages of the invention are set forth below in the following description, or may be learned through practice of the invention.

BRIEF DESCRIPTION OF THE DRAWINGS

A full and enabling disclosure of the present invention is set forth more particularly in the remainder of the specification, including reference to the accompanying figures, in which.

DETAILED DESCRIPTION OF PREFERRED EMBODIMENTS

Definitions

Figure 1:
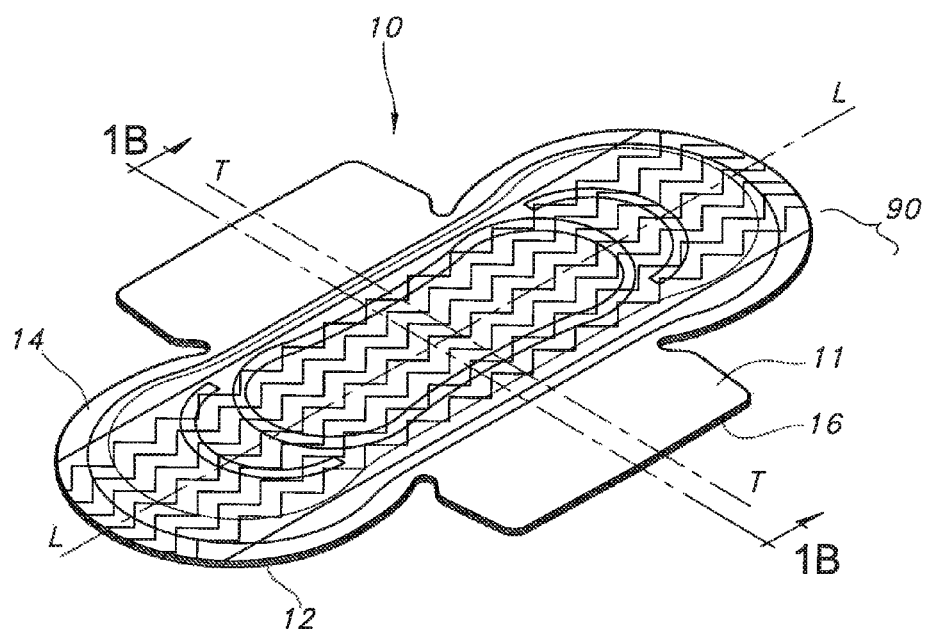
FIG. 1 is a top perspective view of an embodiment of the present invention in the form of a feminine hygienic pad.

As used herein the term "nonwoven fabric or web" refers to a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc. The basis weight of nonwoven webs may generally vary, such as from about 5 grams per square meter ("gsm") to 150 gsm, in some embodiments from about 10 gsm to about 125 gsm, and in some embodiments, from about 25 gsm to about 120 gsm.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki. et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; each of which are incorporated herein in their entirety by reference thereto for all purposes.

As used herein, the terms "decolorizing agent" or "decolorization agent" shall be synonymous and refer to a chemistry or chemical mechanisms which decolorizes blood stains, such as for example, by either filtering or aggregating/binding blood cells from blood-containing fluids, lysing blood cells, causing alteration of the coloring agents from the blood cells, or otherwise chemically altering the perception of color of blood stains through color-changing mechanisms, such as through oxidation or bleaching mechanisms, catalytic oxidation or enzymatic reaction, with the final effect being a decrease or elimination of the red color intensity in certain portions of a feminine care absorbent article and/or fluid flowing out of a feminine care article. Such decolorization agent effectively removes or alters the color of potentially staining fluid, so that fluid which unfortunately travels through or over/across the absorbent article to the article side edges, has less color for staining of garments or bedding, should there be an actual leak of fluid off of the article. By locking up menses coloring agents in particular article areas outside of the absorbent layers, additional absorption of the menses non-colored fluids (lower viscosity clear fluids), may occur throughout dedicated absorbent core areas. For the purposes of this disclosure, decolorization agents are positioned either in or on decolorization agent-containing layers, which are positioned laterally to the central longitudinal axis of the absorbent article and, which extend laterally beyond the longitudinally directed lateral side edges of at least the main absorbent core layer(s) in the article. Such laterally extending decolorization agent-containing layers, can project (as projections) beyond the lateral core edge (that is projecting more laterally towards the article side edge than the core layer(s)), projecting more laterally, from either a layer above the core or below the core (when viewed along the depth axis), or from an attachment to the core itself. As used herein, the term "decolorization agent-containing layer" shall refer to a single layer material, a multiple-layered material structure, a laminate or laminae structure, or a combination thereof, which includes a decolorization agent either in or on its material structure. Examples of laminate-type structures are described in U.S. Pat. Nos. 6,932,929 and 6,896,669 to Woltman, each of which are hereby incorporated by reference in its entirety.

As used herein, the term "masking element" shall refer to the action of obscuring, or the actual physical structure which obscures, such as a material sheet or layer, which obscures the visualization/perception of a blood stain, as opposed to a chemical change which alters the color of the fluid or stain itself. Such a masking element is desirably a film or fibrous hydrophobic barrier material. Such a masking element, for the purposes of this invention, is desirably not absorbent, although it may be liquid permeable. In one embodiment, it would be a nonabsorbent and liquid impermeable material.

As used herein, the terms "superabsorbent polymer," "superabsorbent" or "SAP" shall be used interchangeably and shall mean polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in part on ionicity (a factor of the ionic concentration of the aqueous solution), and the SAP's functional polar groups that have an affinity for water. SAPs are typically made from the polymerization of acrylic acid blended with sodium hydroxide in the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAPs may be present in absorbent articles in particle or fibrous form.

As used herein, the term "menses simulant" refers to a simulated menses fluid which may be used for testing feminine absorbent article products. Such is described for example in U.S. Pat. No. 5,883,231 and in the publication by D, Guralski, Candee Krautkramer, Brian Lin, Jack Lindon, Teuta Elshani, Aneshia Ridenhour, entitled "A Biological Menses Simulant Using a "Batch" Homogenization Process", and published as Document IPCOM000198395D at ip.com, 6 Aug. 2010, each of which are hereby incorporated by reference in their entirety. For the purposes of this disclosure, menses simulant described in these publications was used for evaluation of article performance.

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. For the purposes of this application, like features will be represented by like numbers between the figures. While not being expressly illustrated in every view or location, it should be understood that traditional absorbent article construction adhesive can be used between each of the various article layers, for securement of the layers within the article.

It should be understood that while the main embodiment described herein is a feminine hygiene absorbent personal care article, the present invention is intended to cover all personal care absorbent articles including, but not limited to, diapers, diaper pants, training pants, incontinence devices, feminine hygiene products, bandages and the like. In addition, while the primary body exudate utilized in the description is menses, other body exudates are contemplated including, but not limited to, blood, feces, urine and other body fluids.

Generally speaking, in order to address the staining concerns perceived by consumers from potential pad leakage, to reduce fears of embarrassment from garment or bedding stains resulting from such leakage, and to reduce the effort necessary in removing stains that may actually occur on garments or bedding, the invention provides a feminine hygiene personal care absorbent article with targeted decolorization agents that can render menses stains and menses fluid colorless, or nearly so, within select portions of an absorbent article, before the fluid leaves the article. Such decolorization agents can render such stain or menses fluid, clear or pale yellow, for example, so as to reduce potential staining risk to garments or bedding that may occur. With reduced stain potential, any leakage that actually does occur, will be easier to remove. Additionally, the invention provides decolorization chemistry used in combination with other structural barriers to impede menses flow off of the top surface, or to article side edges and to reduce the visualization of article insult, when viewed from the top surface. The invention provides regions of targeted decolorization chemistry away from the core layer(s) and in some embodiments, separated regions of targeted decolorizing chemistry that are positioned within at least two distinct layers of an absorbent article, which do not impede the direct absorption of menses fluid, once it has entered an absorbent layer, and which layers are positioned away, or directed laterally away from the absorbent layer(s), and projecting laterally towards the product side edges, farther than the lateral side edges of the core layer(s). Of the distinct decolorization agent-containing layers of the article, at least one of such layers is desirably positioned separate from the main absorbent layer structure.

Figure 1A:
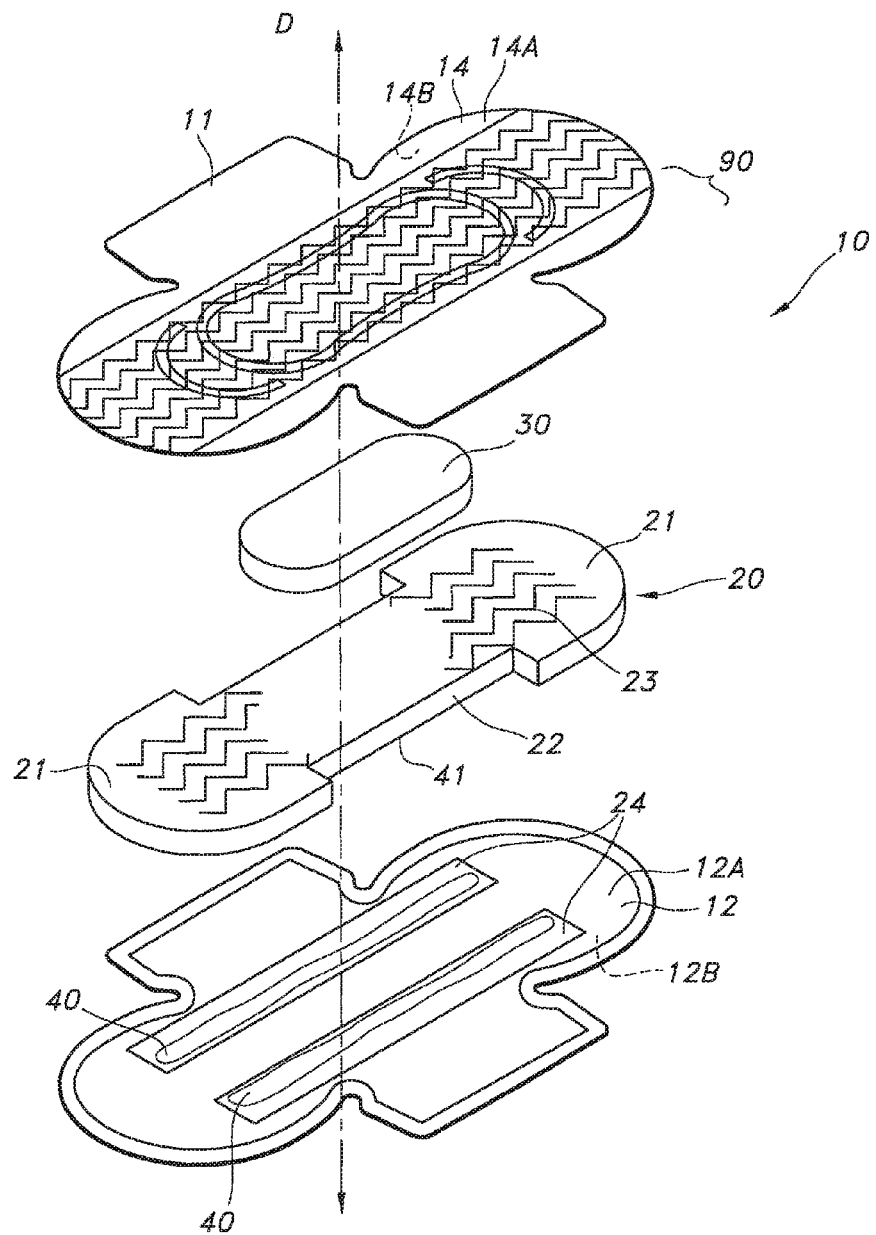
FIG. 1A is a partial exploded perspective view of the pad embodiment of FIG. 1 of the present invention.

More specifically, FIGS. 1 and 1A, illustrate a top perspective and exploded perspective view respectively, of a first embodiment of the present invention in the form of a feminine hygienic pad also referred to as a feminine hygiene absorbent personal care article. The pad has a longitudinal axis (including the central longitudinal axis L shown, as indicated by a broken line), a transverse axis (and a central transverse axis T shown) and a vertical or depth or Z-directional axis D (as seen in FIG. 1A), which is the direction normal to the plane of the pad layers. The feminine hygienic pad (or feminine hygienic absorbent article) 10 has side wings 11 extending out at the longitudinally directed side edges 90 of the article, contains a liquid impermeable garment-facing backsheet layer 12 and a liquid permeable, user facing top layer (e.g., topsheet) 14. The backsheet layer 12 and topsheet layer 14 sandwich at least one absorbent core layer 20. While not expressly labeled, the topsheet layer 14 is shown as including optional embossing patterns in the form of waves/zig-zags, racetrack and arc patterns.

The backsheet layer 12, being generally liquid-impermeable, is designed to face the inner surface, i.e., the crotch portion, of a user's undergarment (not shown) or outer garment. The backsheet therefore includes a core facing surface 12A and an undergarment facing surface 12B. The backsheet layer 12 may optionally permit the passage of air or vapor out of the absorbent article 10, while still blocking the passage of liquids.

Any liquid-impermeable material may generally be utilized to form the backsheet layer 12. For example, one suitable material that may be utilized is a microporous polymeric film, such as a polyolefin film of polyethylene or polypropylene. In particular embodiments, a polyethylene film is utilized that has a thickness in the range of about 0.2 mils to about 5.0 mils, and particularly between about 0.5 to about 3.0 mils. A specific example of a backsheet layer material is a polyethylene film such as that obtainable from Pliant Corporation, Schaumburg, Ill., USA. Another example would include calcium carbonate-filled polypropylene film. In still a further embodiment, the backsheet may be a hydrophobic nonwoven material with water barrier properties such as a nonwoven laminate, an example of which would be a spunbond, meltblown, meltblown, spunbond, four layered, laminate. The backsheet layer 12 may therefore be of a single or multiple layered construction, such as of multiple film layers or laminates of film and nonwoven fibrous layers. Even with a film backsheet, a nonwoven fibrous layer may be used as the undergarment facing surface for better "hand" or feel.

The topsheet layer 14 may surround the absorbent core layer(s) 20 so that it completely encases the absorbent core layer(s) and/or backsheet layer (encasement not shown). Alternatively, the topsheet layer 14 and the backsheet layer 12 may both extend beyond the absorbent core layer(s) 20 lateral-most edges (41, 56, 100 for example) and be peripherally joined together, either entirely or partially, using known attachment techniques. Typically, the topsheet layer 14 and the backsheet layer 12 are joined by adhesive bonding, ultrasonic bonding, or any other suitable joining method known in the art, the sealed edges defining an overall sealed peripheral edge 16 of the feminine hygienic pad 10. The feminine hygienic pad 10 may take on various geometries but will generally have opposite lateral sides (in the product longitudinal direction) and longitudinal ends.

The topsheet layer 14 is generally designed to contact the body of the user and is liquid-permeable. The liquid permeable topsheet layer 14 has an outwardly user facing surface 14A that may directly contact the body of the wearer and receive bodily exudates, and an absorbent layer, facing surface 14B. The topsheet layer 14 is desirably provided for comfort and conformability and functions to direct bodily exudates away from the body of a user, through its structure and towards the absorbent core layer(s) 20. The topsheet layer 14 desirably retains little or no liquid in its structure, so that it provides a relatively comfortable and non-irritating surface next to the tissues within the vestibule of a female wearer.

The topsheet layer 14 can be constructed of any woven, nonwoven or sheet material which is easily penetrated by bodily exudates which contact the surface of the backsheet layer 12. Examples of suitable topsheet materials include natural fiber webs (such as cotton), rayon, bonded carded webs of polyester, polypropylene, polyethylene, nylon, or other heat-bondable fibers, polyolefins, such as copolymers of polypropylene and polyethylene, linear low-density polyethylene, and aliphatic esters such as polylactic acid. Finely perforated films and net materials can also be used, as can laminates of/or combinations of these materials. A specific example of a suitable topsheet material is a bonded carded web made of polypropylene and polyethylene such as that obtainable from Sandler Corporation, Germany. U.S. Pat. No. 4,801,494 to Datta, et al. and U.S. Pat. No. 4,908,026 to Sukiennik, et al. teach various other topsheet materials that may be used in the present invention, each of which is hereby incorporated by reference in its entirety. The topsheet layer 14 may also contain a plurality of apertures (not shown) formed therethrough to permit body fluid to pass more readily into the absorbent core layer(s) 20. The apertures may be randomly or uniformly arranged throughout the topsheet layer 14, or they may be located only in a narrow longitudinal band or strip arranged along the longitudinal axis L of the feminine hygienic pad 10, such as down the central longitudinal axis of the article. The size, shape, diameter and number of apertures may be varied to suit an article's particular needs.

As previously noted, the topsheet layer 14 may also be embossed with any desired embossing pattern to define embossed channels. Embossing techniques are well known to those skilled in the art. An embossing pattern not only creates an aesthetically pleasing surface, but the channels may also facilitate intake of menses fluid. Menses will tend to flow along the densified edges of the channels rather than pool on contact points of the topsheet layer 14.

The topsheet layer itself may also be formed from one or more layers in a side-by-side arrangement along the longitudinal axis, as will be described in connection with FIGS. 1B, 1C, 1D, 1K and 1L. Desirably, in one embodiment, the topsheet layer has a basis weight of between about 15 gsm and 100 gsm.

Figure 1B:
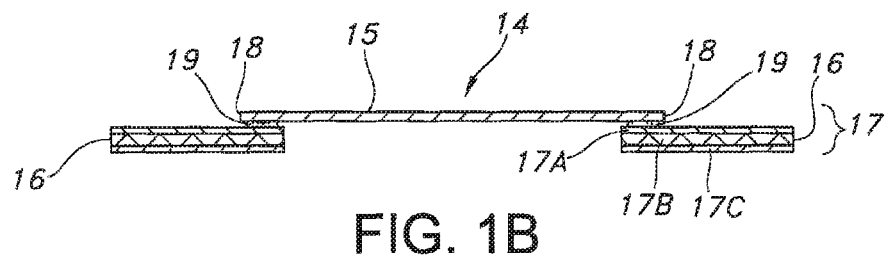
FIG. 1B is a cross-sectional view of one embodiment of the topsheet of the pad embodiment of FIG. 1, taken along line 1B-1B.

In one embodiment, as seen in the cross-sectional view of the topsheet layer 14 of FIG. 1B, taken along lines 1B-1B of FIG. 1, the topsheet layer 14 is constructed of at least two different materials 15, 17 in an overlapping, but substantially side-by-side arrangement along the longitudinal axis. Such a dual-layer construction is generally described in U.S. Pat. No. 5,961,505 to Coe, U.S. Pat. No. 5,415,640 to Kirby and U.S. Pat. No. 6,117,523 to Sugahara, each of which is incorporated by reference herein in its entirety. With specific reference to FIG. 1B, in one embodiment, a central longitudinally directed topsheet material 15 is positioned along the central longitudinal axis L of the topsheet layer 14. Such central longitudinally directed topsheet material 15 is desirably through air bonded carded web materials (TABCW) having a basis weight of between about 15 and 100 gsm. Previously described nonwoven, woven and film topsheet materials may also be used as the central longitudinally directed topsheet material 15 of the topsheet layer 14. In one embodiment, such central longitudinal material is constructed from TABCW having a basis weight of between about 20 and 50 gsm, which are readily available from nonwoven material manufacturers, such as Xiamen Yanjan Industry, Beijing DaYuan Nonwoven Fabrics and others. Different nonwoven, woven or film sheet materials may be used as the longitudinally directed side edge topsheet materials 17, adjacent and bonded to the central longitudinally directed topsheet material 15. The selection of such topsheet layer 14 materials will vary based on the overall desired attributes of the topsheet. For example, it may be desired to have a hydrophilic material along the central longitudinal axis and hydrophobic barrier-type materials along the longitudinal side edges to prevent leakage and increase a sensation of dryness at those longitudinal side edges. Such longitudinally directed side edge materials 17 may be either adhesively, thermally, ultrasonically or otherwise bonded 19 to the central longitudinally directed material topsheet 15 along the longitudinally directed side edges 18 (on the absorbent core layer facing surface 14B) of the central longitudinally directed topsheet material 15. Such longitudinally directed side edge topsheet materials 17 may be of a single or multiple-layered construction. In one embodiment, such longitudinally directed side edge topsheet materials 17 are themselves adhesively bonded laminates, which include decolorizing agent chemistry. In one embodiment, for example, such longitudinally directed side edge topsheet materials 17, are constructed of an upper nonwoven layer 17A, such as a meltblown microfiber material (MBMF as further described), middle layers of decolorizing agent chemistry 17B and bonding adhesive 17D (as seen in FIG. 1E), and a bottom layer 17C of a hydrophobic barrier film. In such a configuration, the upper meltblown polypropylene microfiber material is desirably between about 10 and 100 gsm in basis weight, having a fiber size of desirably of between about 1 and 10 microns in diameter. Such material is available from Yuhan-Kimberly Corporation, Seoul, Korea. Because these meltblown materials are inherently hydrophobic, they are desirably treated with wetting agents for adequate handling of aqueous fluids such as menses. Examples of such wetting agents include surface active agents (or surfactants) having a hydrophilic lipophilic balance (HLB) of at least 6, preferably between 7 and 18. Definitions of "surfactant" and "HLB scale" can be found in textbook "Introduction to Colloid and Surface Chemistry", by Duncan J Shaw, $4^{th}$ edition, 1992, published by Butterworth-Heinemann, Ltd. A variety of surfactants can be used and include those that are anionic, cationic or neutral from a charge standpoint. Mixtures of surfactants and other wetting agents can also be used. Typical wetting agent add-on can range between, about 0.1 to 10 wt %, preferably between 0.2 to 5% by weight of the substrate. However, add-on levels higher than 10 wt % can also be used. These wetting agents can have an effect of moving aqueous fluids through a porous media such as a microfiber meltblown and/or a multilayered laminate, but also, it has been found, that only certain wetting agents can decolorize fluids such as menstrual fluid. However, the extent of decolorization depends on the type of wetting agent. The decolorizing agent on such a nonwoven layer is desirably in one embodiment a polyethylene glycol (PEG), applied via slot die coating ("slot coating") process in an amount of between about 10 and 30 gsm. Such a PEG is exemplified by PEG 8000 Carbowax Sentry. Other coating processes such as saturation, spray, kiss roll and printing can also be used.

The construction adhesive is desirably used to laminate the meltblown microfiber layer at an add-on of between about 1 and 5 gsm and the film barrier layer is desirably a polyolefin film of a basis weight of between about 10 and 40 gsm. In such laminate embodiments including both decolorization chemistry and adhesive, the decolorization chemistry and adhesive may be employed in a single layer, or in separate layers (as seen specifically in FIG. 1E). Traditional article construction adhesive may be used to bond the longitudinally directed side edge topsheet materials 17 to the central longitudinally directed topsheet material 15. Desirably, such decolorizing agent chemistry is applied to the meltblown layer 17A using a saturation technique such as a spray, foam, slot die or kiss roll. Such is desirably applied in an amount of between about 3 and 60 gsm. In such an embodiment, it is desirable for such decolorizing chemistry to be either applied on top of the meltblown on the body-facing side or sandwiched between layers. Such decolorization agent application may be across the entire surface of the meltblown layer (decolorization agent-containing layer) or alternatively in a stripe pattern along the length of the strip, with untreated zones between stripes of decolorization agent. If such striping treatment is employed, such stripes may be used to create decolorized regions between non-decolorized regions on the strips, serving as pad saturation warning indicators to consumers. In such a fashion, decolorization of potentially staining fluid would be accomplished by the article, as well as providing a visual warning (through the appearance of colored and non-colored stripes) to the consumer of impending pad saturation.

In an alternative embodiment, different concentrations of a decolorization agent can be applied in the stripes on a strip so that filtering occurs in a graduated scale across the transverse direction of the strip. In still a further alternative embodiment, different decolorization agents can be used in different stripes on the strip, for similar reasons. When a film barrier layer 17C is used in the overall topsheet design, it may include opacifying agents, such as film pigments, that help the film in masking stains along or adjacent to, the pad's side edges 90. In such a fashion the film layer would serve as a masking element in the pad to limit visualization of a menses insult stain along the central, longitudinal axis L of the pad. The film layer may also serve as a barrier layer to prevent rewet of the topsheet layer user facing surface, as well as to prevent the flow of menses to the side edges of an article. Such film layer may in some embodiments include apertures, such as to allow one-way directional transfer of fluid to the core layer.

Figure 1C:
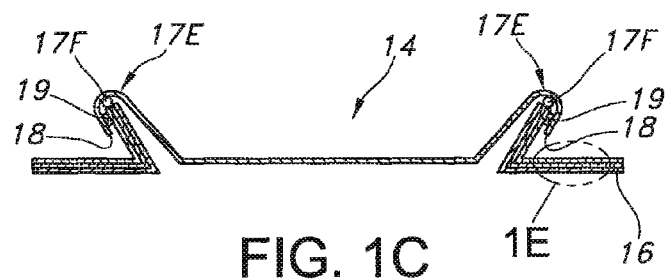
FIG. 1C is a cross-sectional view of an alternative embodiment of the topsheet of the pad embodiment of FIG. 1, taken at approximately the same position as lines 1B-1B.

As seen in FIG. 1C, in an alternative embodiment, such topsheet layer 14 may include topographical features 17E which extend out of the overall plane of the topsheet layer 14, and which result from side portions of the topsheet layer rising above the generally planar surface, either as a result of contracted elastic strands, or shrinkable yarns 17F that are laminated to the topsheet layer along the longitudinal axis L, and which shrink upon lamination or alternatively, during contact with menses/moisture. Such strands or yarns, while being shown in two locations in the Figure, may be placed in several (typically parallel) longitudinally directed configurations, across the transverse axis of the article. Such a configuration is described for example, in U.S. 20100152690 to Ong, which is hereby incorporated by reference in its entirety.

Figure 1D:
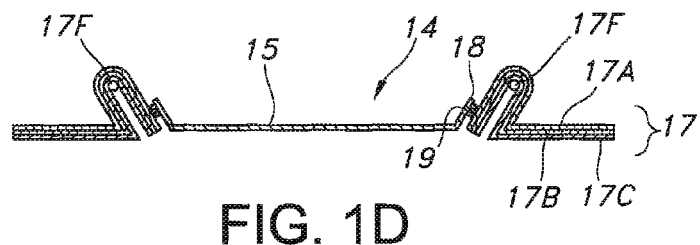
FIG. 1D is a cross-sectional view of an alternative embodiment of the topsheet of the pad embodiment of FIG. 1, taken at approximately the same position as line 1B-1B.
Figure 1E:
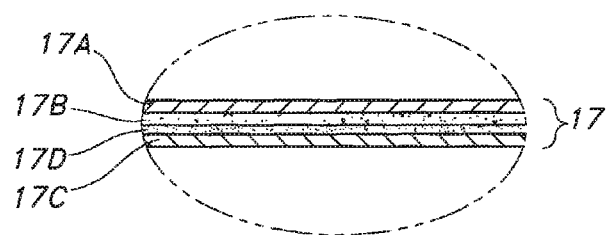
FIG. 1E is an enlarged partial cross-sectional view of an embodiment of the topsheet side material in the embodiment of FIG. 10 with the center topsheet material layer removed.

In still a further alternative embodiment of a topsheet layer 14, as seen in the cross-sectional view of FIG. 1D, instead of the central longitudinally directed topsheet material 15 wrapping over the edges of the longitudinally directed side edge topsheet materials 17 and bonded thereto 19, (as seen in FIG. 10), it may instead be bonded 19 adjacent the edge. In this fashion, the longitudinally directed side edge topsheet materials 17 would make up the majority of the raised feature on the topsheet layer 14.

The feminine hygienic pad 10 of FIGS. 1 and 1A also contains at least one absorbent core layer 20 positioned between the topsheet layer 14 and the backsheet layer 12, that provides capacity to absorb and retain bodily exudates. The one or more absorbent core layers 20 may be selected so that it/they demonstrate a particular total absorbency capacity, depending on the article type. For example, for feminine care products, the total absorbency capacity can typically be within the range of about 7-50 grams of menstrual fluid, and can more typically be within the range of about 30-40 g of menstrual fluid. Within the feminine care hygienic article category, it may be desirable to have different levels of absorbency capacity depending on product type. For example, feminine care panty liners are typically used by consumers for "light" menstrual flow days, feminine care pads are typically used by consumers for "regular" menstrual flow days, and feminine care oversized pads are typically used by consumers for "overnight" timespans, or "heavy" menstrual flow days. It may be desirable for feminine care liners to have in one embodiment, an absorbency capacity of between about 1 and 5 grams of fluid. For feminine care pads, it may be desirable in one embodiment, to have an absorbency capacity of between about 10 and 30 grams of fluid. For feminine care oversized pads, in one embodiment it may be desirable to have an absorbency capacity of between about 20 and 50 grams of fluid.

The one or more absorbent core layers 20 can generally be any single layer structure or combination of layer components, which desirably demonstrate some level of compressibility, conformability, are non-irritating to a wearer's skin, and capable of absorbing and retaining liquids and certain other body wastes. For example, the absorbent core layer(s) 20 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In a particular embodiment, the absorbent web material is a matrix of cellulosic fluff, and may also include superabsorbent material. The cellulosic fluff may comprise a blend of wood pulp fluff. One desirable type of fluff is identified with the trade designation NB 416, available from Weyerhaeuser Corp., and is a bleached, highly absorbent wood pulp containing primarily soft wood fibers. The absorbent materials may be formed into a web structure by employing various conventional methods and techniques. For example, the absorbent web may be formed with a dry-forming technique, an air forming technique, a wet-forming technique, a foam-forming technique (making a foam or foam-like structure), or the like, as well as combinations thereof. A coform nonwoven material may also be employed. Methods and apparatus for carrying out such techniques are well known in the art.

As illustrated in FIG. 1A, in one embodiment, the absorbent core layer 20 optionally includes longitudinally directed front and rear bulbous portions 21 and indented or cut-out portions in the core 22 along the core side longitudinal edges 41. For the purposes of this invention, such indented or cut-out portions 22 are not structurally necessary, but desirable for a compact core design. The core layer 20 may also optionally include an embossing feature 23 for fluid management benefits, or layer stability when wet. In the embodiment illustrated, such embossing feature 23 is not present along the longitudinal and transverse axis central areas of the absorbent core layer 20. Such embossing feature may also be present in the center of the absorbent core layer if desired. Such core layer may be wrapped in tissue for integrity.

Figure 1F:
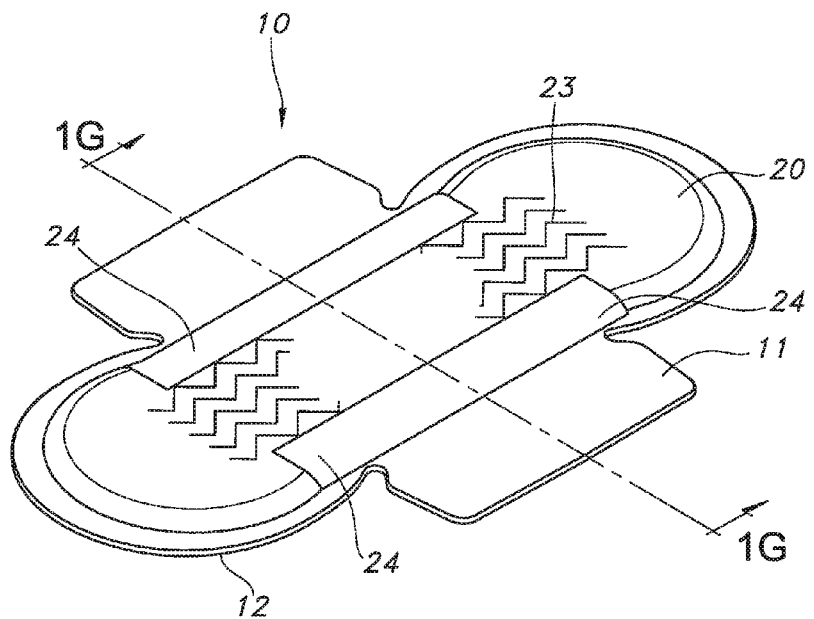
FIG. 1F is a partial top perspective view of the embodiment of FIG. 1 with the topsheet layer and airlaid layer removed.
Figure 1G:
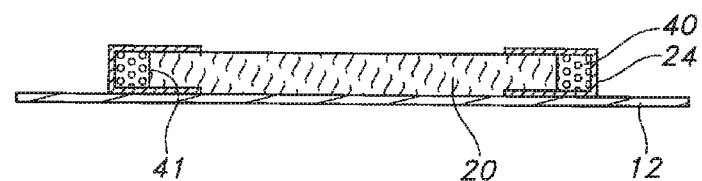
FIG. 1G is a cross-sectional view of the partial pad embodiment of FIG. 1F, taken approximately along line 1G-1G.
Figure 1H:
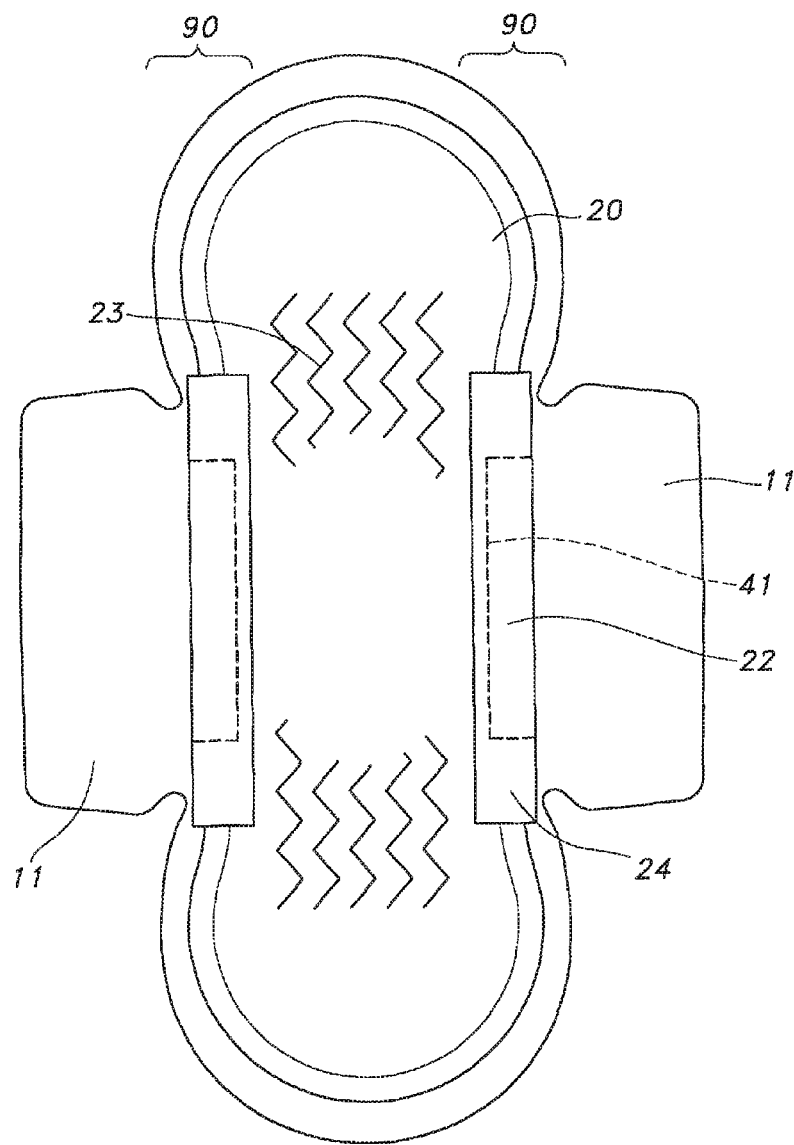
FIG. 1H is a top plan view of FIG. 1F.

In one embodiment of the core layer, nonwoven side core-edge wraps 24 are initially positioned on the core-facing surface 12A of the backsheet layer 12 for wrapping about the side longitudinally directed edges of the absorbent core layer 20 and for containing a decolorization agent, whether or not the core layer includes cutout or indented portions 22. Such nonwoven side core-edge wraps are desirably constructed from meltblown microfiber webs as previously described. A wide variety of side core-edge wrap materials is envisaged such as nonwoven sheets, film sheets or laminates thereof. Such material is in one embodiment, wrapped about the side edges of a cellulosic fluff-based absorbent core layer 20 in the finished product, and holds a decolorizing agent 40, (as seen in FIGS. 1A and 1G). It should be understood that in an alternative embodiment (not shown) the side core-edge wraps 24 may be wrapped about a non-indented core layer edge as well. A side perspective view of the partial product can be seen in FIG. 1F with the side core-edge wraps 24 folded over the user facing surface of the core layer 20. A cross-sectional view of the partial product of FIG. 1F, taken along lines 1G-1G, can be seen FIG. 1G. As can be seen in FIG. 1G, side nonwoven core-edge wraps 24 hold a decolorizing agent 40 close to the longitudinal side edges 41 of the absorbent core layer 20. Such placement of the decolorizing agent does not interfere with the flow of exudates into the core layer, and decolorizes such exudates before such fluid can exit from the longitudinal side edges of the core layer (at the narrowest dimension of the product). A top plan view of a partial product, without a topsheet and having a wrapped core, wrapped by side core-edge wraps 24, and with the core layer including indented side edges 22, shown in broken lines, can be seen in FIG. 1H. The wrap 24, which is in one embodiment a meltblown microfiber material of polypropylene (MBMF), is desirably treated with decolorization agent chemistry 40, such as ammonium sulfate, at an add-on of between about 40 and 120 gsm, alternatively between about 60 and 100 gsm. In one embodiment, such wraps 24 are of a dimension of between about 2 and 6 inch in length and between about 0.5 and 2 inch in width. In a further embodiment, such wraps have a basis weight of between about 10 and 100 gsm, desirably between about 20 and 50 gsm, more desirably about 30 gsm.

Figure 1I:
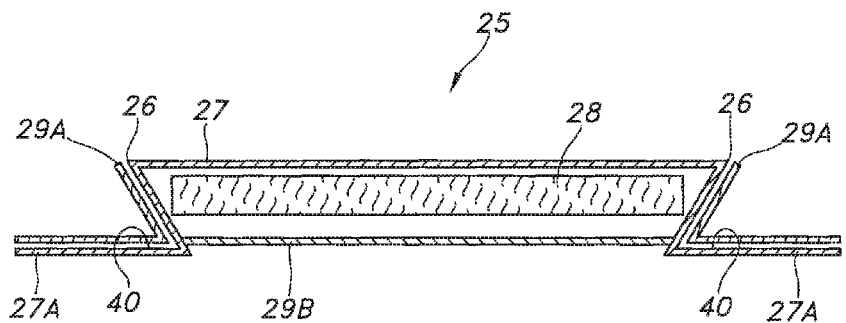
FIG. 1I is a cross-sectional view of an alternative core structure for the pad embodiment of FIG. 1, and is a replacement for the indented core with wrap-around decolorization agent containing wraps shown specifically in FIG. 1A.

In a further alternative embodiment, as illustrated in FIG. 1I, a main absorbent core layer 25 may include a Z-folded structure along its longitudinally directed side edges. Such a structure includes decolorizing agents 40 placed along its longitudinally directed side edges, between layers 29A and 27A. As can be seen in FIG. 1I, the overall core layer 25 includes side edge Z-fold features 26. In this structure, it is desired that the main absorbent core layer 25 include an upper-most layer 27 that faces the topsheet layer in use (topsheet layer not shown). Such a core structure may be immediately adjacent the topsheet layer, or alternatively adjacent an intermediate transfer layer. Such upper-most layer 27 is desirably an airlaid structure of with bonded fibers that yield an average pore size between 1 and 500 microns, and having a basis weight of between about 40 and 200 gsm. Such upper-most layer 27 partially envelops the lower absorbent layer 28 at the side edges. The shape of the overall core layer 25 from a top plan view (not shown) is desirably a rectangular or dogbone shape, as is known in the art. The longitudinal side edges of the upper-most layer 27 are folded so as to partially envelop or wrap around a lower absorbent layer 28, that is desirably a superabsorbent polymer (SAP)-containing sheet. Desirably, such superabsorbent polymer-containing sheet is a fluff-based material that is a combination of pulp and SAP enclosed with a tissue carrier and having a basis weight of between about 40 and 400 gsm. Positioned to the sides edges 29A and also immediately under 29B the lower absorbent layer 28 (superabsorbent polymer-containing sheet), is a barrier film layer, desirably of between about 10 and 40 gsm, more desirably about 10 gsm, and made from traditional film-forming polymers such as polyolefins such as polyethylene. Such side film layers 29A are folded with the airlaid layer to create the Z-configuration seen in FIG. 1I. The film layers are bonded to the sides of the airlaid layer and the bottom surface of the lower absorbent layer 28. Such layers would also be bonded to the backsheet layer (not shown) or any layer between the backsheet layer and the core layer. The film layers are desirably opaque, and include opacifying pigments in sufficient quantity (as is known in the film art) to obscure the view of any stain present beneath them in the underlying airlaid layer 27A. It should be recognized that the individual layers in this alternative absorbent core layer 25 may be bonded using traditional bonding techniques such as thermal, ultrasonic or adhesive processes, within the core layer itself 25, then bonded using any of such methods to the remaining absorbent article structure. Such alternative core layer structure directs any insult of the layer with menses that is not held within the lower absorbent layer 28, to flow along the Z-fold structure. By flowing along the Z-fold, menses stains are both masked by the film layers 29A from the top view by the Z-configuration (when viewing from through the topsheet), and decolorized along the sides via the decolorizing agents 40. It should be recognized that while not being shown in this figure, a backsheet layer 12 would similarly be positioned beneath (along the D axis) and adjacent the film layer 29B and airlaid layer 27A. It should be appreciated that any staining within the absorbent core layer 25 of this embodiment is masked from the topsheet layer view, making any insult look centralized within the article, and having relatively clean longitudinal side edges. Any leakage of a menses insult from the longitudinally directed side edges of such core would also be decolorized before exiting the feminine hygienic pad. As an alternative to this embodiment, such film layers 29A and 29B may be replaced with a fibrous material, or chemically treated fibrous material, designed to impart a hydrophobic barrier. Such alternative core layer structure 25 can be used in conjunction with any of the previously described topsheets or in a further embodiment, with any type of traditional topsheet layer, such as with a homogenous apertured film or permeable nonwoven layer.

Figure 1J:
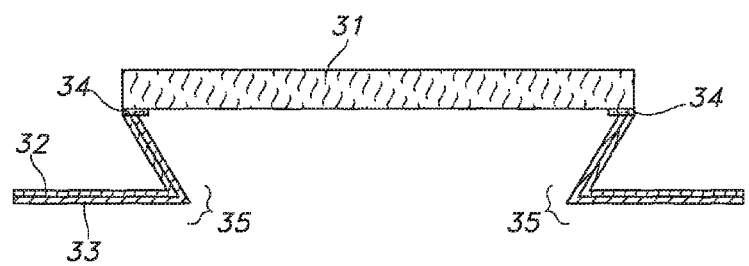
FIG. 1J is a cross-sectional view of a further alternative core layer structure for the pad embodiment of FIG. 1, and is a replacement for the indented core with wrap-around decolorization agent containing wraps, shown specifically in FIG. 1A.

In still a further alternative embodiment of an absorbent core layer structure for use in the feminine hygienic pad of FIG. 1, a cross-sectional view of an absorbent core layer construction is illustrated in FIG. 1J. While the top plan view of such a structure can be rectangular or dogbone shaped as previously described (and not shown), the cross-sectional view of the alternative embodiment includes a main absorbent layer 31, which is adhesively or otherwise bonded 34 along the side longitudinal edges of its garment facing surface, to a V-folded 35 nonwoven 33 and film layer 32 laminate. Such V-folded laminate is essentially a laterally directed projection off of the core layer. In such an embodiment, the main absorbent core layer 31 may be any traditionally employed absorbent material, such as a fluff-based, airlaid, or SAP containing compressed core. Desirably in such an embodiment, a film masking layer 32 is positioned along the inner surface of the V-fold. Such film layer may be of any traditional barrier film materials, but desirably in one embodiment is of a polyethylene at about 10 gsm. Alternatively, the basis weight of such film layer is between about 10 and 40 gsm. As with previously described masking film layers, this film layer can include masking pigments to obscure the view of the stain when viewed from the topsheet layer. Laminated to the film by any known method, is desirably a decolorization agent-treated nonwoven layer. In such an embodiment, the treated nonwoven agent is desirably a latex bonded airlaid web or a meltblown microfiber web having a basis weight of between about 20 and 150 gsm. In such a core structural configuration, stain masking and decolorization can both be achieved by the core structure (as also described with respect to the immediately preceding embodiment) but in a less complex core design. Such alternative core layer structure can be used in conjunction with any of the previously described topsheets or in a further embodiment, with any type of traditional topsheet layer, such as with a homogenous apertured film or permeable nonwoven layer. While shown in a raised configuration for ease of viewing, the absorbent core layer 31 and lower side, V-folded laminates 35 actually would be desirably bonded to a lower layer (such as the backsheet layer) in practice of the embodiment. The V-folded laminates 35 may, for the purposes of this invention also be described as U-folded.

In either of the alternative absorbent core layers described above (FIGS. 1I and 1J), such layers act to delay the spread of a menses insult from reaching the side edges of the absorbent article. This delay can result in an increase in actual absorbency of the absorbent core and at the same time, provide masking along the side edges of the pad to address consumer emotional concerns over extensive menses pad staining.

Figure 1K:
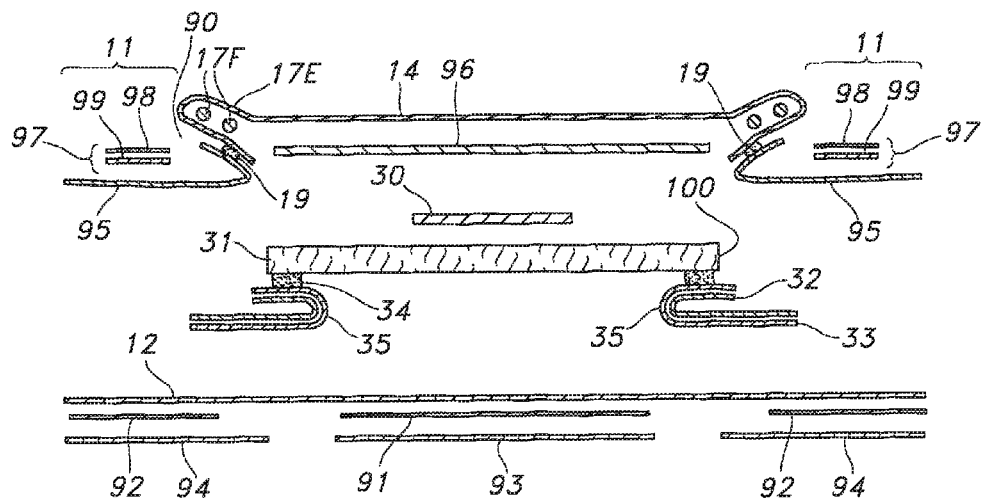
FIG. 1K is a cross-sectional view of a further alternative embodiment of the hygienic pad layers of FIG. 1.

In still a further alternative embodiment of the hygienic pad of FIG. 1, as can be seen in FIG. 1K, a cross-sectional view of various pad layers is shown. The pad includes a topsheet layer 14, and a backsheet layer 12. Subjacent the backsheet layer 12 in the D axis direction, are found garment fastening adhesive patches 91 and 92. The garment adhesive patch 91 is situated along the pad central longitudinal axis of the garment facing surface of the backsheet, for fastening directly to the crotch portion of an undergarment. The two side wing adhesive patches 92 are positioned under the wings 11, also on the garment facing surface of the backsheet. Adhesive peel/release sheets 93, 94 are positioned respectively over the garment adhesive patch 91, and the wing adhesive patches 92. The topsheet layer 14, includes a topographical/raised feature 17E raised in part by shrinkable fibers 17F. The topsheet layer 14, wraps around the longitudinally directed shrinkable fibers 17F and is bonded to side nonwoven topsheet layers 95 via at least bond points or bond lines 19. Desirably, the side nonwoven topsheet layers are either a film and spunbond nonwoven laminate, a spunbond-meltblown-meltblown-spunbond layer laminate, or alternatively, a hydrophobic nonwoven material. Other types of materials have been previously described. Atop such side layers are desirably placed a laminate 97 of a decolorization agent-treated nonwoven strip 98 that is laminated to a masking element, such as a film layer 99 or other hydrophobic nonwoven layer, having the same dimensions. Such laminate 97 is placed along the longitudinal side edges of the pad in a configuration that places it adjacent the side edges 90 of the pad and over a portion of the wing 11. Desirably, such nonwoven strip layer 98 is an MBMF layer that is treated with a decolorization agent, such as about 10 to about 30 gsm of high molecular weight PEG, by either slot coating or spray application. Such treated strip is desirably between about 5 to 60 mm in width along the pad's transverse axis/direction, and would extend laterally out to cover both the pad longitudinal side edges 90 and a portion of the wings 11. Such a MBMF layer is desirably treated with a wetting agent and PEG. It is desirable that such strips extend the entire length of the article, but a shorter strip would also function. Such shorter strips in an alternative embodiment would extend between about 30 and 100 percent of the length of the article. While it is most desirable to add such strips along the side longitudinal edges of the article, they can in an alternative embodiment, be added in shortened lengths across the ends of the article in the transverse direction, to reduce leakage stain potential from the ends of the article. In still a further alternative embodiment, they may be added along all edges of the article. Alternatively, rather than place the strips above the topsheet material, such strips may be placed below the topsheet materials, above the core layer(s) in the same general locations. Such treated nonwoven and film laminate 97 includes a film layer for masking purposes and positions the film layer facing the topsheet side nonwoven layers 95. In one embodiment, the film masking layer is an apertured film. In alternative embodiments, such masking layer can be an opaque and hydrophobic nonwoven layer. As illustrated in FIG. 1J, an absorbent layer 31 is positioned adjacent an additional airlaid layer 30. The absorbent layer 31 is adhesively bonded 34 to a film and treated nonwoven laminate, having a film layer 32 positioned along the inside of a U-shaped or V-shaped decolorization agent-containing layer configuration 35 along the longitudinal axis of the article, and extending laterally outward of the side edges 100 of at least the main absorbent core layer, and desirably all absorbent core layers, if more than one. Such U-shaped or V-shaped decolorization agent-containing layer is a laterally directed projection off of the core layer. Such projections can be positioned either off of the garment-facing surface or the topsheet-facing surface of the core layer. The treated nonwoven layer 33 is positioned in the illustrated embodiment, along the outside of the U-shaped or V-shaped configuration 35. The nonwoven layer can be in one embodiment, either an airlaid layer or a MBMF layer as previously described and is desirably treated with between about 20 and 200 gsm of a decolorization agent such as a salt. In one embodiment, the salt is desirably ammonium sulfate. The absorbent core layer 31 is desirably a fluff layer, airlaid layer or SAP sheet. An airlaid layer 30 is desirably positioned between the topsheet layer 14 and the absorbent core layer 31. Additionally, a bicomponent fluid distribution layer (BFDL) 96 is positioned between the airlaid layer 30 and the topsheet layer 14.

Figure 1L:
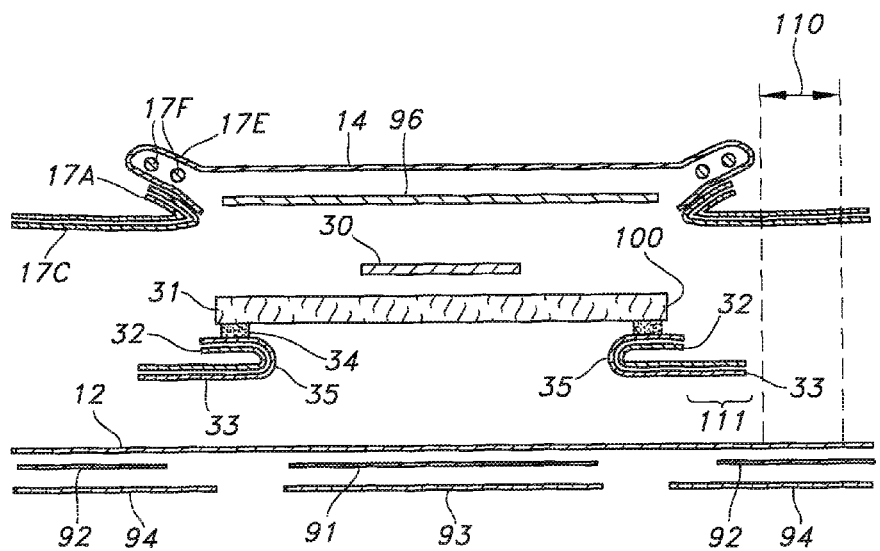
FIG. 1L is a cross-sectional view of a further alternative embodiment of the hygienic pad layers of FIG. 1.

In still a further alternative embodiment of the pad of FIG. 1, as can be seen in FIG. 1L and which shows a cross-sectional view, instead of having a separate decolorization agent layer/film masking layer laminate attached adjacent the longitudinal side edges of side topsheet layer materials 95 (as in FIG. 1K), the decolorization agent layer/film masking layer laminate themselves make up the topsheet side layers (as seen in FIGS. 1B, 1C, and 1D). Other structures are similar to those present in FIG. 1K. As can be seen in FIG. 1L, the decolorization agent layer in the topsheet side layers 17A, 17C, and U-shaped decolorization layers extending laterally off of the core lower surface 32, 33 (adjacent the backsheet layer 12) each extend laterally towards the side edges of the article and towards the wings 11. In particular, the topsheet side edge materials extend toward the side edges and wing areas at 110, and the U-shaped decolorization layers extend laterally off of the core lower surface towards the article side edge and wings, past the lateral edges of the core layer 111 situated above it along the D axis. In this fashion, for embodiments illustrated in FIGS. 1K and 1L, there are two separated decolorization agent-containing layers, each of which are part of laminates with masking layers (although masking layers not required), each of which are not contained within the main absorbent layer of the article (so as not to impede the flow of menses within the main absorbent layers), and each of which extend beyond the lateral side edges 100 of the core layer(s) of the article in the transverse axis direction.

As can be seen from the various embodiments described above, the decolorization agent layers of the various embodiments extend laterally beyond the longitudinal side edges of the main absorbent core layers 20, 28, 31 (laterally beyond the core longitudinal side edges when viewed along the D-axis). In many embodiments, such decolorization agent-containing layers also include masking layers laminated thereto to provide such pads with both potential leakage decolorization (in two vital areas of the pad), as well as stain masking.

As noted from the various embodiments, the feminine hygienic pad 10 may also contain additional layers. For example, in one embodiment, the feminine hygienic pad 10 may contain a liquid-permeable intake layer positioned between the topsheet layer 14 and the absorbent core layer 20. A seen in FIG. 1A, the feminine hygienic pad 10 includes an additional absorbent airlaid layer 30. Such an intake layer may be made of a material that is capable of rapidly transferring, in the D-direction, body fluid that is delivered to the topsheet layer 14. The intake layer may generally have any shape and/or size desired. In one embodiment, the intake layer has a rectangular shape, with a length equal to or less than the overall length of the feminine hygienic pad 10, and a width less than the width of the feminine hygienic pad 10. For example, a length of between about 150 mm to about 300 mm and a width of between about 10 mm to about 60 mm may be utilized. Any of a variety of different materials are capable of being used for the intake layer to accomplish the above-mentioned functions. The material may be synthetic, cellulosic, or a combination of synthetic and cellulosic materials. For example, airlaid cellulosic tissues may be suitable for use in the intake layer. The airlaid cellulosic tissue may have a basis weight ranging from about 10 gsm to about 300 gsm, and in some embodiments, between about 100 gsm to about 250 gsm. In one embodiment, the airlaid cellulosic tissue has a basis weight of about 200 gsm. The airlaid tissue may be formed from hardwood and/or softwood fibers. An airlaid tissue has a fine pore structure and provides an excellent wicking capacity, especially for menses.

Additional layers between the topsheet layer and the core layer include liquid-permeable transfer delay layers or surge layers as are commonly known. Still another layer that may be present between the topsheet layer and the absorbent core layer includes a bicomponent fluid distribution layer (BFDL), which increases absorbency by providing a high void space and may be made of a TABCW, having a basis weight in one embodiment of between about 25 and 100 gsm. While side wings 11 are shown as formed from extensions of the backsheet 12 and the topsheet 14 such that they are integral portions of the pad 10, they may also be later-attached, non-integral structures. As an additional, but optional feature to the embodiments described, lines of polymeric material may be applied along the edges of, or adjacent the edges, of any of the described layers (not shown). Such polymeric material may be applied to either the user facing surface or the garment facing surface of the layers, so as to create an additional hydrophobic barrier to stop or retard the flow of a spreading menses stain.

Figure 2:
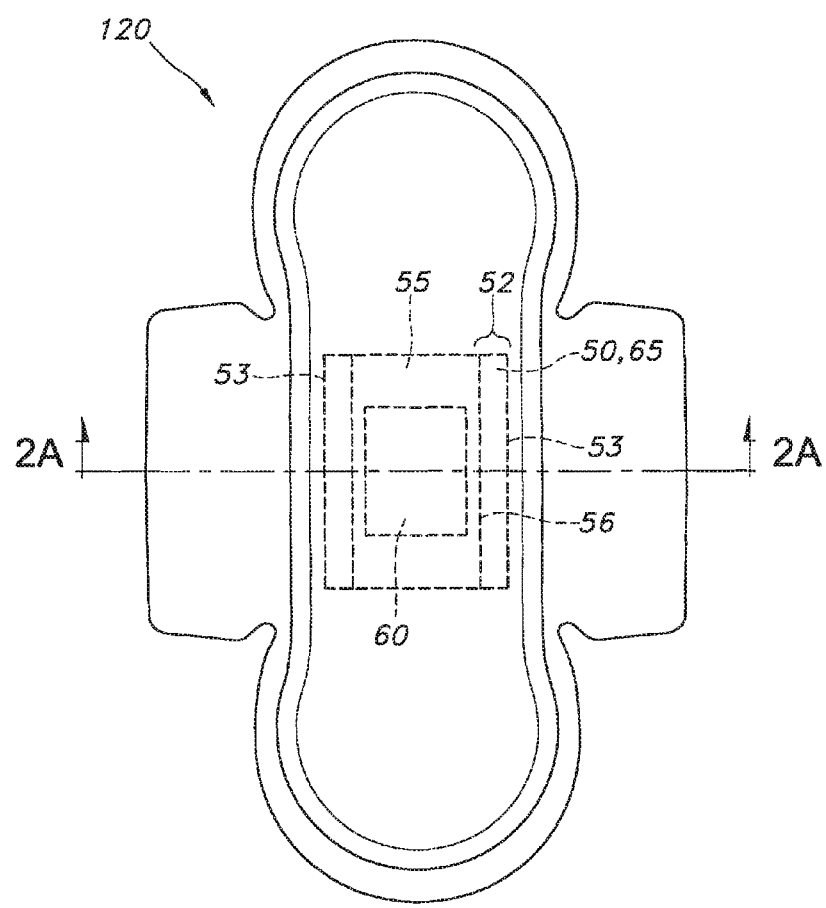
FIG. 2 is a top plan view of an alternative embodiment of a feminine hygienic pad of the invention.
Figure 2A:
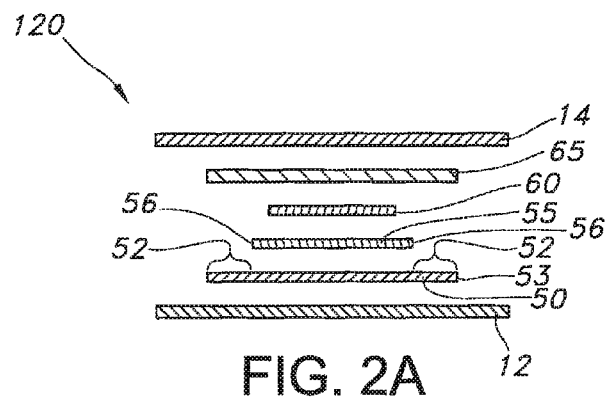
FIG. 2A is a cross-sectional view of FIG. 2 taken along line 2A-2A.

In still a further alternative embodiment of a feminine hygienic pad of the invention, as seen in the top plan view of FIG. 2 and respective cross-sectional view in FIG. 2A taken along line 2A-2A of FIG. 2, the targeted decolorization agents may be applied to multiple discrete and separated layers of an absorbent core structure. As seen in FIG. 2A, for example, the feminine hygienic pad 120 includes a backsheet layer 12 and a topsheet layer 14. In one embodiment, a BFDL layer 65 is positioned adjacent to the topsheet layer 14. Adjacent to the BFDL layer 65 is positioned a multifunctional airlaid layer 60. Adjacent the multifunctional airlaid layer 60 is positioned a traditional fluff-based core layer 55. The fluff-based core layer 55 may in one embodiment, be treated throughout its structure with a decolorization agent, or alternatively treated with such an agent along the longitudinal side edges 56 only. Adjacent the traditional fluff-based core layer 55 is positioned a decolorization agent-treated carrier layer 50. Such carrier layer may be made from a variety of known materials, such as for example, a nonwoven layer or a foam layer that has been treated either throughout its structure, or along the longitudinal side edges 53 with a decolorization agent. In one embodiment, the carrier layer has a basis weight of between about 50 and 200 gsm. In a further embodiment, the length and width dimensions of the BFDL layer are the same as the carrier layer. In still a further embodiment, the decolorization agent is treated on the carrier layer 50, only at locations 52 on the carrier layer which are outside of the peripheral dimensions of the fluff-based core layer 55 which is situated above it along the D axis. In this fashion, as a menses insult travels through an absorbent core structure to its peripheral edges, it is decolorized at or past its peripheral edges by either the outer edges of the core or by the carrier layer, such that any leakage of the pad along the pad's longitudinally directed side edges would be devoid of significant color or nearly colorless.

It should be recognized that in still a further alternative embodiment of the invention, the structures described in FIGS. 2 and 2A can also be used in conjunction with topsheet layer configurations described in the previous figures.

In this fashion, decolorization agents are desirably separated into two or more distinct decolorization agent-containing layers within the product, and as desired, may be employed along with masking elements and optionally polymeric barrier materials. Such decolorization-agent, containing layers are positioned laterally from the core layers and/or initial fluid deposition regions (along the central longitudinal axis of the article), such that absorbency pathways are not hindered within the article. It should also be recognized that multiple types of decolorization agents may be employed in a single absorbent article. In still a further alternative embodiment of the article, the overall width in the transverse direction, between the lateral most edges of the decolorization agent containing layer (such as strips, layer or projections) is larger than the absorbent layer(s), or alternatively, larger than any superabsorbent-containing layer(s). That is, the width in the transverse direction between one lateral edge to the other of the decolorization agent containing layer(s) (such as between outer lateral edge of strips, projections or carrier layer), is desirably greater than the width of the absorbent layer(s) or superabsorbent-containing layer(s).

By employing the structural embodiments described herein, a decolorization region is created at or near the pad's lateral periphery that is treated with the decolorizing agent. In this manner, the decolorizing agent helps to discharge color from potentially stain-producing exudates at the edges of the product, and desirably off of the topsheet layer, where leakage is most likely to occur in modern feminine-hygiene absorbent articles. Interior regions of the product may be left substantially untreated with the decolorization agents, thereby, allowing the decolorizing agents to target menses at specific peripheral structures. This enables a user to observe and inspect the bodily exudates in the center of the product, and also allows the decolorizing agents to be applied only to those portions of the product needed to achieve the desired effect so that the untreated regions can continue to fulfill their functions, such as absorbing or wicking fluids, etc. without undue stiffness or sacrifice in comfort. In addition, the use of targeted decolorizing agents in conjunction with masking structures (if desired) provides additional emotional comfort to users who prefer not to view the spread of menses insult stains, and while also seeking comfort in knowing that leakage that may result from such pad will result in less visibly apparent staining on a garment or bedding.

Desirable decolorizing agents to be used in conjunction with the structural embodiments described herein, include a wide array of chemistries. While known decolorizing agents may be used, it is desirable that the decolorizing agents be selected from the following categories of chemistries, for the following reasons.

In one embodiment of the invention, the decolorization agent is desirably a menses filtration chemistry, i.e., an agent that can precipitate, coagulate, phase separate components, or otherwise demonstrate an affinity to the red components of menses. Such a chemistry may be applied/treated on one or more of the described layers of the feminine hygiene absorbent article. It has been found that when menses insults the treated material, the red component of the menses, composed of red blood cells and the protein hemoglobin, is rendered insoluble in an aggregate form, and is retained by the layer of the article, while only a clear or slightly colored solution that is relatively innocuous to staining, leaches from the insulted area. Therefore, any side leakage from a pad, or rewet (that is, fluid flowing back out of the pad from the topsheet surface), demonstrates a clear appearance or reduced coloration.

It has therefore been found that in one embodiment, polyethylene glycols or PEGs and polyethylene oxides or PEOs having average molecular weights of between about 300 and 2,000,000, alternatively, between about 500 and 2,000,000, alternatively between about 1000 and 1,000,000, alternatively between about 1000 and 400,000, alternatively, between about 1000 and 100,000, alternatively between about 3000 and 100,000 are desirable for use with this invention. In another embodiment, PEGs or PEOs having average molecular weights between about 3000 and 35,000 are desirable. As the ethylene oxide chain impacts functionality of the invention, PEG variants with different functional groups on each end will also be acceptable for use in the invention. Linear as well as branched forms will likewise be acceptable for use in the invention. For example, higher molecular weight methoxypolyethylene glycols or MPEGs similarly have such an effect that is MPEGs having a molecular weight greater than or equal to about 750. These ranges demonstrated noticeable discoloration of menses from surrounding fluid. Still in a further embodiment, PEGs having average molecular weights of between about 4000 and 12000 are desirable. Finally, other chemical derivatives, such as Cetiol-HE will have similar effects as PEG and thus are contemplated to be within the scope of the invention.

The relative percentages of add-on, and add-on level in gram per square meter (gsm) or in weight percent (wt %) of the composition with respect to a dimension of the base substrate (area or weight) may vary to achieve the desired level of decolorization. The "add-on level percentage with respect to weight" is determined by subtracting the weight of the untreated substrate from the weight of the treated substrate (after any optional drying steps), dividing this calculated weight by the weight of the untreated substrate, and then multiplying by 100 wt % to produce a weight (wt) percent, in some embodiments involving PEG, PEO and mPEG decolorization agent chemistry, the add-on level of the decolorizing agents is at least about 15 wt %, alternatively, at least about 25 wt %, in some embodiments from about 15 to 190 wt %, and still in another alternative from about 50 wt % to about 200 wt %.

The add-on level in gsm of the composition is the actual added dried weight (in grams) to the same area of the initial substrate. Desirably, substrate add-on levels can range from about 5 to 150 gsm. In an alternative embodiment, such add-on levels can range from about 5 to 100 gsm, and in still further embodiments from about 4 to 40 gsm, or still further from about 60 to 100 gsm. In particular, for a PEG with 8000 molecular weight, treatment at about 5 to 40 gsm or alternatively between about 50-100 gsm add-on level is desirable.

Since the higher molecular weight PEGs are solids, they can be melted and applied onto nonwoven substrates by slot coating or spray applications. Alternatively, PEGs may be placed in solvents such as water or alcohol and applied by spraying, dipping or various printing methods. Such applications to nonwovens may be uniform or nonuniform. Since higher add-on levels of such chemistries have a higher decolorization effect, but also impact absorbency, it is also desirable to place such decolorization agents in predominantly nonabsorbent layers, or at the periphery of either the absorbent article or of absorbent layers. Such PEG and PEO materials are available from the Dow Chemical Company under the trade name CARBOWAX and CARBOWAX SENTRY, Sigma Aldrich, and Acros Organics.

Additional menses filtration chemistry that can be used in conjunction with the structural invention include surface active agents ("surfactants") such as those that are based on polyether siloxane chemistry. Examples of polyether siloxanes, also referred to as dimethicone copolyols, include but are not limited to MASIL SF 19, available from Emerald Performance Materials, LLC, Cheyenne, Wyo., and Dow Corning 193C Fluid ("DC193C") and Dow Corning Q2-5211 Superwetting Agent ("Q2-5211"), both available from Dow Corning, Midland, Mich. Other surfactants that can be used include ethoxylated fatty esters such as hydrogenated ethoxylated castor oil. Another family of surfactants that may be used include those in the alkyl polyglycoside ("APG") category, such as those described in U.S. Pat. No. 6,060,636 which is hereby incorporated by reference thereto in its entirety. An example of such surfactants include Glucopon 220 UP and Standapol 215 UP, available from Cognis Corp. of Cincinnati, Ohio. Another example of a surfactant that may be used as a decolorization agent includes, Cirrasol PP 862 (formerly known as Ahcovel Base-N 62) from Croda, Inc.

As with the PEGs, PEOs, and derivatives thereof, such as methyl end-capped PEG's (or MPEG's), it has been found that a broad range of surfactants and wetting agent add-on levels may be used in conjunction with the invention, as described above.

It has also been found that denser or variable density fibrous layer substrates may further enhance the filtration effects of the chemical filtration agent materials as well. In particular, it has been found that the substrate and chemistry can be manipulated to create a synergistic filtration effect. It is observed that two factors of the base substrate contribute to the filtration effect, the first being the pore size of the substrate, and the second being the wicking capability of the substrate. Therefore several substrates may be desirable embodiments for use as a decolorization-agent containing layer. A hydrophilically treated meltblown microfiber substrate is desirable, based on pore size and wicking abilities. Further, multiple layers of PEG-treated nonwoven materials, such as airlaid materials, can be bonded together in a staggered format to also enhance the filtration effect. By staggered, it is meant that a piece of material is joined to another with some overlap, but also with some spacing between layers. The staggered nonwoven increases the flow path of the menses in the same manner of a high wicking/highly porous substrate, thereby increasing the filtration efficiency of the PEG. Such a combination can enhance the stain barrier function of the substrate, thereby limiting the visual stain spread to a certain region, allowing clear or almost clear fluid only, to pass out of the denser substrate area. In further alternative embodiments of the article, several decolorization-agent containing layers may be separated by physical gaps or spaces, or one or more layers within the article, or alternatively, placed one upon the other (immediately adjacent one another in the depth direction) of the article. Such separation would assist in the lateral and longitudinal wicking/distribution of the menses stain in the article.

In order to test the PEG chemistry for its intended usage, the following experiments were conducted:

Experimental Examples

General procedure for producing high molecular weight PEG-treated and related chemistry, substrates:

Different average molecular weight-sized PEGs were applied to nonwoven materials by soaking the nonwoven samples and subsequently air-drying, with 5, 10, 15, 20, 25, 30% (w/w) PEG solution in water on a 60 gsm latex-bonded pulp-based, single-layered airlaid substrate (Sambo, Korea). The add-on was from 0.37 to 0.40 grams of PEG. PEGs were obtained from Dow Chemicals, in granular or flake form under the trade name CARBOWAX, from Sigma Aldrich, and from Acros Organics. First the PEG was dissolved in distilled water at 20% concentration. The airlaid was dipped in the PEG solution, excess liquid was removed by suspending it in mid-air for 15 minutes and then the airlaid sample was dried in an oven set to 80 C in a flat state for 2 hours. Alternatively, the sample was allowed to air dry for two days. The obtained and treated sheets were tested to observe the discoloration by filtration on the sheets. For the purposes of these experiments, filtration of the sheets was conducted by dropping 0.1-0.3 grams of menses simulant, or alternatively 200 ul, dropwise from a pipette onto the sheets. The sheets were then examined to see if there was a discoloration gap or zone in the stain as it wicked on the substrate which resulted from the plasma (clear fluid) separating from the red blood cells or hemoglobin. For the purposes of these experiments, add-on was calculated as the percentage of basis weight of PEG added divided by the basis weight of the base material.

- 3015-3685 average molecular weight PEG (Sigma Aldrich) treated sheets showed a partial decolorized gap (1 mm) from menses colored regions, from 90% add on level up to 190% (approximately 2 mm). Higher add on level of PEG gave wider discoloration gap (1-2 mm) but no more than 2 mm gap, and became more stiff on the sheet, the higher level of add-on being used.
- 7000-9000 average molecular weight PEG (Acros Organic) treated sheet showed a partial decolorized gap (less than 1 mm) from menses colored regions, from 60% add on level up to 190%. Higher add on level of PEG showed wider discoloration gap (1-2 mm) but no more than 2 mm gap, and became more stiff of the sheet, the higher level of add-on being used.
- 16000-24000 average molecular weight PEG (Sigma Aldrich) treated sheet showed a partial decolorized gap from menses colored regions, from 60% add on level up to 190%. Higher add on level of PEG showed wider discoloration gap (1-2 mm) but no more than 2 mm gap, and became more stiff of the sheet, the higher level of add-on being used.
- 35000 average molecular weight PEG (Sigma Aldrich) treated sheet showed a partial decolorized gap from menses colored regions, from 60% add on level up to 190%. Higher add on level showed wider discoloration gap (1-2 mm) but no more than 2 mm gap, and became more stiff of the sheet, the higher the level of add-on being used.

In the tests with different molecular weight PEGs, the higher molecular weight PEGs required less add on amount for the same discoloration of menses simulant, but it was noted that for PEGs having a molecular weight above 8000, the differences were insignificant in filtration observation. It was also noted that the solubility of PEG in aqueous medium decreased significantly with increased molecular weight. As more time was needed for the PEG to solubilize, the discoloration gap was reduced.

Melt blown micro fiber sheets (MBMF of polypropylene) were also used in the experiments, having a basis weight of 50 gsm. It should be noted however, that MBMF webs of 20 and 60 gsm are also available. The sheets were supplied by Yuhan-Kimberly Corporation Korea, and also available from Fiber-Tex, Malaysia. The sheets were hydrophilically treated by either Aerosol GPG of Cytec, or alternatively Ahcovel Base N-62.

In particular, a 50 gsm hydrophilically treated MBMF sheet was treated with 3015-3685 average molecular weight PEG and 7000-9000 average molecular weight PEG by soaking and air-drying with 30% (w/w) PEG solution in water, which gave 130% or 106% add-on amount on the MBMF respectively. These sheets were tested for discoloration by filtration on the sheets of the menses simulant. A resulting higher discoloration gap (3-5 mm) was demonstrated. Additionally, the resulting meltblown material appeared softer than the pulp-based airlaid.

MPEG was also tested for its ability to decolorize menses. In particular, the same general testing procedures were employed. MPEG was obtained from Dow Chemical having a molecular weight of about 750. A 15 wt % mPEG solution was prepared. The airlaid or MBMF substrates were dipped in the solution and dried in the air. A few drops of simulant (1-3 drops) were placed on the mPEG-treated substrate and after a couple of minutes, clear fluid was observed along the peripheral areas around the simulant in the substrate.

In a further embodiment, carbomer and salt chemistry has been found to successfully separate menses coloring agents from non-colored menses portions. In particular, the decolorization agent for a decolorization agent-layer, is selected from the group of trichloroacetic acid, ammonium sulfate and acrylate polymers (carbomers) or combinations thereof, with the optional addition of non-ammonium sulfate salts. It has been found that such materials are particularly desirable treatments to be placed specifically on or adjacent an absorbent core layer, or alternatively, on a carrier layer to be placed between an absorbent core layer and a backsheet layer. Such a carrier layer may be selected from foams, sponge-like networks, nonwovens such as tissue layers, wovens or particles, and would desirably extend beyond the lateral side edges of the absorbent core layer(s), such as shown in FIG. 2A. For nonwoven carrier layers, such as tissues, in one embodiment it is desirable for such basis weight to be between about 50 and 150 gsm. For foam-type carrier layers, in one embodiment it is desirable for such basis weight to be between about 100 and 200 gsm.

An effective combination for use on an absorbent core layer or carrier layer is a mixture of an acrylate polymer and a salt. Examples of such an acrylate polymer that is desirable includes carbomer available through Lubrizol, Ohio and Spectrum Chemicals of New Jersey and California. Carbomers from other vendors and suppliers may also be used. Specific examples of desirable carbomers include Carbopol ETD 2020, Carbopol Ultrez 21, Carbopol 980 NF, and Carbopol 1342 NF of Lubrizol. Examples of salts to be used with such acrylate polymer include sodium chloride, magnesium chloride, potassium chloride and ammonium sulfate.

For this chemical combination, a suspension of the carbomer and a solution of salt may be prepared by mixing in water and stirring until a suspension is achieved. Suggested dispersion techniques are further described on the Lubrizol corporate websites. In one embodiment, an acceptable range of such a combination would be between about 0.1% to 1% carbomer and between about 4 and 20% salt. Such may desirably be applied onto a fibrous material or open cell foam (or foam-like material) and dried. A substrate is loaded with this combination as described and then, if loaded on a carrier layer, placed adjacent to the absorbent core layer of an absorbent article (such as between the core layer and the backsheet layer). In this fashion, any absorbed menses slowly comes into contact with the decolorization agent and undergoes decolorization, without impacting the absorbency level of a core layer. Over a period of time, the decolorized menses is separated onto the treated substrate. The red color is confined to the center of the pad, if applied to either a centrally positioned core layer or carrier layer, and a relatively colorless liquid is allowed to pass beyond the core, should leakage actually occur. Desirably in one embodiment, the chemistry is applied to a substrate using a dip and squeeze or spray method and in add-on levels/amounts of carbomer between about 9 and 33 gsm, NaCl between about 17-78 gsm, and ammonium sulfate of between about 16-310 gsm. In a desirable embodiment, an absorbent core layer is treated by a dip or spray method with between about 50 and 300 gsm ammonium sulfate and a foam carrier layer is treated by a dip or spray method with about 20 gsm NaCl and between about 11-16 gsm carbomer. Such carrier layer may have a similar dimension to a BFDL contained in the article and extends beyond the peripheral dimensions of the absorbent core layer at least along the longitudinal side edges (lateral sides) of the core layer.

Carbomer Experimental Examples

In several experiments, a nonwoven material such as tissue or meltblown material, or foam was dipped in a suspension consisting of 0.7% Carbopol ETD 2020 and 8% NaCl and allowed to be shaken on an orbital shaker for approximately 10 minutes. The material was removed with a tweezer and excess fluid was removed by gently holding it over a sink. The material was then transferred to a polypropylene mesh for drying. Alternatively, for thin nonwoven samples, the material was first laid flat on the polypropylene mesh and then sprayed with the treatment solution via a spray bottle. As with the previous method, excess fluid was allowed to run off in a sink area. Regardless of treatment methods, the treated materials were allowed to be dried in an oven at between about 50-60° C. For foam materials, the drying temperature was maintained below 60° C.

Once completely dried, the materials were removed and used for testing. The treated materials were laid under an absorbent core layer, with a nonwoven intake layer positioned on top of the absorbent core layer. The treated-material dimensions extended beyond the absorbent core layer such that they were readily visible when viewed from above, and could be seen extending beyond the edges of the overlaid absorbent core layer. The samples were placed on a weight scale and between about 5 and 10 g of menses simulant was insulted on top of the nonwoven intake layer by using a plastic transfer pipette and slowly dropping simulant in a central region until the desirable insult weight was achieved. The menses simulant was then allowed to absorb to the core from the fluid transfer. After 1 to 2 hours or more, filtration of the coloring components of the menses simulant was observed, such that clear fluid wicked to the treated material side edges (as observed at least along the treated material top surface), while red-staining occurred at the core layer center in the initially soiled region. It was observed that the amount of wicked fluid increased with increasing time and insult amount.

Zinc-Oxide Experimental Examples

In a further embodiment of the invention, a zinc-oxide suspension in water and surfactants, has been found to adsorb (and thus filter out) the red protein contained in menses. It has been found that for such a system to be successful, it is desirable for acidifying agents to be present in the layered structure to keep the relative pH at a desired level of between about 3 and 6. Additionally, zinc-oxide must be stably bound to a layer substrate. As a result, in one embodiment a zinc-oxide decolorization mixture, the mixture includes zinc-oxide particles, a surfactant to disperse zinc-oxide, an acidifying agent, a binder for attaching such zinc-oxide to a nonwoven or other material substrate and a solvent. Such a mixture can be applied to a substrate in one step, rather than through a multiple step process. Desirably in such a suspension, the zinc-oxide is present in an amount of between about 0.1 wt % and 20 wt %, more desirably in an amount between about 0.5 wt % and 10 wt %, a surfactant is present in an amount of between about 0.1 wt % and 20 wt %, more desirably between about 0.5 wt % and about 10 wt %, an acidifying agent is present to create a pH range of between 3 and 6, a binder is present in an amount of between about 0.1 wt % and 10 wt %, more desirably between about 0.5 wt % to 5 wt %. An example of such ZnO particles include Solaveil CZ-300 from Croda (Edison, N.J.), Zinc-Oxide from NanoScale Materials, Inc., Manhattan, Kans. Examples of such surfactants include DC 193 C from Dow Corning (Midland, Mich.) and Ahcovel Base N-62 from ICI. In one embodiment, superwetting agents are more desirable, such as a siloxane polyether. Examples of such acidifying agents include lactic acid from Sigma Aldrich (Milwaukee, Wis.). Examples of such binders include Chitosan such as Hydagen HCMF from Cognis (Cincinnati, Ohio). Desirably, such mixture has an add-on of between about 0.2 and 20 wt % to a variety of substrate materials, including microfiber meltblown and other nonwovens and laminates having similar capillary structures. Such Zinc-oxide mixture can also include other functional chemistries as desired, such as for example, preservatives, anti-oxidants, scents, pigments and anti-microbial agents. Further, rather than Zinc-oxide, other metal oxides such as silica can be used, also at lower pH environments. Such application is desirably applied to a substrate using spray, saturation, slot die, foam and printing methodologies.

Zinc-Oxide Formulations:

Samples were prepared from meltblown microfiber nonwovens at 35 gsm. The meltblown layer was treated via saturation (dip and squeeze methods) using a lab wringer and the samples were allowed to dry at typically 80° C. for 1 hour or until a constant weight was reached. The material was treated at an add-on level of about 10 weight percent. Menses was contacted to such samples by depositing a 2 ml droplet of menses simulant.

Formulation 1

| Purpose | Ingredient | Wt % | Wt (g) |
| --- | --- | --- | --- |
| Zinc-oxide/Anti-stain | Solaveil CZ-300 | 2 | 4 |
| Surfactant | Ahcovel Base N 62 | 4 | 8 |
| Emulsifier | Standapol 215 UP | 2 | 4 |
| Surfactant | DC 193 C | 2 | 4 |
| Solvent | Water | 90 | 180 |
|  |  | 100 | 200 |

Formulation 2

| Purpose | Ingredient | Wt (g) | Wt % |
| --- | --- | --- | --- |
| Surfactant | DC 193 C | 2.00 | 2.00 |
| Zinc Oxide/Anti-stain | ZnO | 0.50 | 0.50 |
| Acid/pH control | Lactic acid | 1.00 | 1.00 |
| Solvent | Water | 96.50 | 96.50 |
|  |  | 100.00 | 100.00 |

Formulation 3

| Purpose | Ingredient | Wt (g) | Wt % |
| --- | --- | --- | --- |
| Surfactant | DC193 C | 1.00 | 1.00 |
| Binder | HCMF | 0.20 | 0.20 |
| Acid/pH control | Lactic acid | 1.00 | 1.00 |
| Solvent | Water | 97.80 | 97.80 |
|  |  | 100.00 | 100.0 |

Formulation 4

| Purpose | Ingredient | Wt (g) | Wt % |
| --- | --- | --- | --- |
| Surfactant | DC 193 C | 1.00 | 1.00 |
| Binder | HCMF | 0.50 | 0.50 |
| Acid | Lactic acid | 1.00 | 1.00 |
| Zinc-oxide/Anti-stain | ZnO | 0.25 | 0.25 |
| Solvent | Water | 97.25 | 97.25 |
|  |  | 100.00 | 100.00 |

For each of the above formulations, menses simulant was successfully filtered, as red colorant was visually observed as being isolated from surrounding fluid spread. However, for formulation 3, good fluid wicking properties were observed but decolorization was not as pronounced as in other examples where ZnO was present. In one embodiment it is desirable to include such ZnO mixture as a treatment on topsheet side materials or side core-edge wrap materials.

Each of such filtration chemistries described above can be used in a further embodiment, with a line of polymer barrier applied to one or more layers. Such a polymer barrier may be placed on a substrate, such as for example, peripheral portions of the absorbent layer or the side edge and core wrap substrates described previously in FIGS. 1B-1D, 1G, 1I and 1J. Essentially, such polymeric barrier may be applied in a discontinuous or desirably continuous, line or strip to an article layer, thereby creating a physical barrier material to block menses flow. Such a polymer barrier may include a co-polymer system that contains a mixture of hydrophilic and hydrophobic monomers that are water soluble, but act as a barrier when applied to a substrate. Examples of such polymers include acrylic acid, 2-acrylamido-2-methylpropane-sulfonic acid and sodium salt, n-butyl acrylate and 2-ethylhexyl acrylate. Such a mixture could include surfactants or amphiphilic molecules such as sodium lauryl sulfate and disodium lauryl sulfosuccinate. Water insoluble polymers may include for example acrylates (C12-22), alkyl methacrylate copolymer, and acrylate/octylacrylamide copolymer. It has been found that application of such materials still allow for a level of softness in a substrate. Such polymer barrier may be applied in one embodiment by printing or spray of 5 to 20% solution (w/w) in alcohol at an add-on level of between about 0.1% and 20%. Desirably, such polymer is applied at 1% to 10%, and between about 0.5 and 10 mm from the lateral side-most edges of the article.

A variety of techniques may be used for applying the decolorizing agent compositions to either a predominantly nonabsorbent carrier substrate. For instance, the decolorizing agent composition may be applied using rotogravure or gravure printing, either direct or indirect (offset). Gravure printing encompasses several well-known engraving techniques, such as mechanical engraving, acid-etch engraving, electronic engraving and ceramic laser engraving. Such printing techniques provide excellent control of the agent composition distribution and transfer rate. Gravure printing may provide, for example, from about 10 to about 1000 deposits per lineal inch (2.54 cm) of surface, or from about 100 to about 1,000,000 deposits per square inch (2.54 cm$^2$). Each deposit results from an individual cell on a printing roll, so that the density of the deposits corresponds to the density of the cells. A suitable electronic engraved example for a primary delivery zone is about 200 deposits per lineal inch (2.54 cm) of surface, or about 40,000 deposits per square inch (2.54 cm$^2$). By providing such a large number of small deposits, the uniformity of the deposit distribution may be enhanced. Also, because of the large number of small deposits applied to the surface of the substrate, the deposits more readily re-solidify on the exposed fiber portions. Suitable gravure printing techniques are also described in U.S. Pat. No. 6,231,719 to Garvey, et al., which is incorporated herein in its entirety by reference thereto for all purposes. Moreover, besides gravure printing, it should be understood that other printing techniques, such as flexographic printing, may also be used to apply the composition.

Still another suitable contact printing technique that may be utilized in the present invention is screen printing." Screen printing is performed manually or photomechanically. The screens may include a silk or nylon fabric mesh with, for instance, from about 40 to about 120 openings per lineal centimeter. The screen material is attached to a frame and stretched to provide a smooth surface. The stencil is applied to the bottom side of the screen, i.e., the side in contact with the substrate upon which the composition is to be printed. The decolorizing composition is painted onto the screen, and transferred by rubbing the screen (which is in contact with the substrate) with a squeegee.

Ink-jet printing techniques may also be employed in the present invention. Ink-jet printing is a non-contact printing technique that involves forcing the ink through a tiny nozzle (or a series of nozzles) to form droplets that are directed toward the substrate. Two techniques are generally utilized, i.e., "DOD" (Drop-On-Demand) or CIJ (continuous ink-jet) printing. In CIJ systems, ink is emitted in a continuous stream under pressure through at least one orifice or nozzle. The stream is perturbed by a pressurization actuator to break the stream into droplets at a fixed distance from the orifice. DOD systems, on the other hand, use a pressurization actuator at each orifice to break the ink into droplets. The pressurization actuator in each system may be a piezoelectric crystal, an acoustic device, a thermal device, etc. The selection of the type of ink-jet printing system varies on the type of formulation used and material to be printed from the print head. For example, low viscosity formulations (e.g. 2 cps) are sometimes required for CIJ printing systems while higher viscosity formulations 2 cps) can be used with a DOP printing system.

In addition to the printing techniques mentioned above, any other suitable application technique may be used in the present invention. For example, other suitable printing techniques may include, but not limited to, such as laser printing, thermal ribbon printing, piston printing, spray printing, flexographic printing, etc. Still other suitable application techniques may include bar, roll, knife, curtain, spray, slot-die, dip-coating, drop-coating, extrusion, stencil application, etc. Such techniques are well known to those skilled in the art.

Regardless of the method of application, the substrate may sometimes be dried at a certain temperature to drive any solvent from the decolorizing composition. For example, the treated substrate may be heated to a temperature of at least about 8° C., in some embodiments at least about 12° C., and in some embodiments, at least about 15° C. Generally required drying temperature is dependent on level of solvent (e.g. water) present on the substrate following treatment and on the line speed during a typical continuous production process. In other words, a temperature is applied for a dwell time that is necessary to flash off the solvent. By minimizing the amount of solvent in the decolorizing composition, a larger amount of agent may be available for contacting bodily exudates, thereby enhancing its ability to decolorize hemoglobin or other colored substances contained in menses exudates.

It has been found that feminine pad leakage often results from residual pad menses insults on or near the topsheet layer, user-facing surface of a pad. Such residual insult either is not contained by the absorbent layer(s) as a result of fluid saturation of the layer or impeded flow of an insult into the absorbent structure. By "impeded", it is meant that such flow is either slowed or restricted as a result of the absorbent layer structure, or alternatively, not absorbed quickly enough as a result of a sudden insult. Such impeded flow can result in run-off of insult from the pad, even when the absorbent layer is not saturated. When an absorbent layer is saturated, the menses insult can pool on the surface of the pad which can subsequently run off the side edges of the pad to a garment or bedding, or be transferred via body contact to a garment or bedding. As runoff and pooling are often the immediate causes of staining in thinner feminine pads, the described invention has addressed such causes by directing fluid flow not only in absorbent layers, but also in non-absorbent layers at side edges of a pad.

As has been described herein, the body exudate and specifically the menses may be altered in its visual appearance and physical characteristics due to the use of decolorizing agent chemistry (such as, for example, the PEG and other chemistries described herein) and decolorizing materials (such as, for example, the MBMF and other materials described herein) which may be collectively referred to as "decolorization means" 89 (see FIGS. 3-7) and the decolorization agent chemistry and the decolorizing materials may be used alone or in combination with one another. Alternatively, they may be used separately from one another in various locations within or on the article as described herein.

The net effect of using the decolorization means 89 is to increase the performance of the article 10 and instill in the wearer a greater degree of confidence and peace of mind that the product is performing as designed and that if an accident such as a leak or spill was to occur, that there would be less stress and embarrassment associated with such a leak or spill. A better understanding of these benefits can be obtained with reference to FIGS. 3 through 7 of the drawings.

As has been shown in the previous embodiments and drawings, the decolorization means are typically located such that they extend outboard of all or a portion of the peripheral edge of the absorbent core 20 so as to not impede the fluid handling capabilities of the absorbent core. See for example, FIGS. 1F, 1G, 1H and 1I of the drawings. In FIGS. 1F and 1G, the decolorization means is shown as elements 24 and 40 which are located at and outboard of the lateral side edges of the absorbent core 20. In this embodiment the decolorization means overlaps the top and bottom surfaces of the absorbent core as well as the lateral side edges of the absorbent core 20. In addition, it is desirable that the decolorization means also extends laterally outboard of the absorbent core 20. If desired, these decolorization means may completely surround the peripheral edge of the absorbent core. Alternatively, the decolorization means can be located in opposed longitudinal end portions of the article and not be present in the lateral side portions and conversely, they may be located in the opposed lateral side portions and not located in the longitudinal end portions. Alternatively or in combination with such location of the decolorization means, the decolorization means may be used on the top or user facing surface of the topsheet layer. See for example, FIGS. 1C, 1D and 1E of the drawings. In FIGS. 1C, 1D and 1E the decolorization means is a combination of the MBMF layer (element 17A) and a decolorizing agent chemistry (element 17B). Finally, such decolorization means may be used in any combination of the foregoing areas of the article 10 including the topsheet layer 14. In these configurations, the decolorizing means rises up above the user facing surface of the product to create dams that will restrict and decolorize the lateral flow of exudates such as menses.

Figure 3:
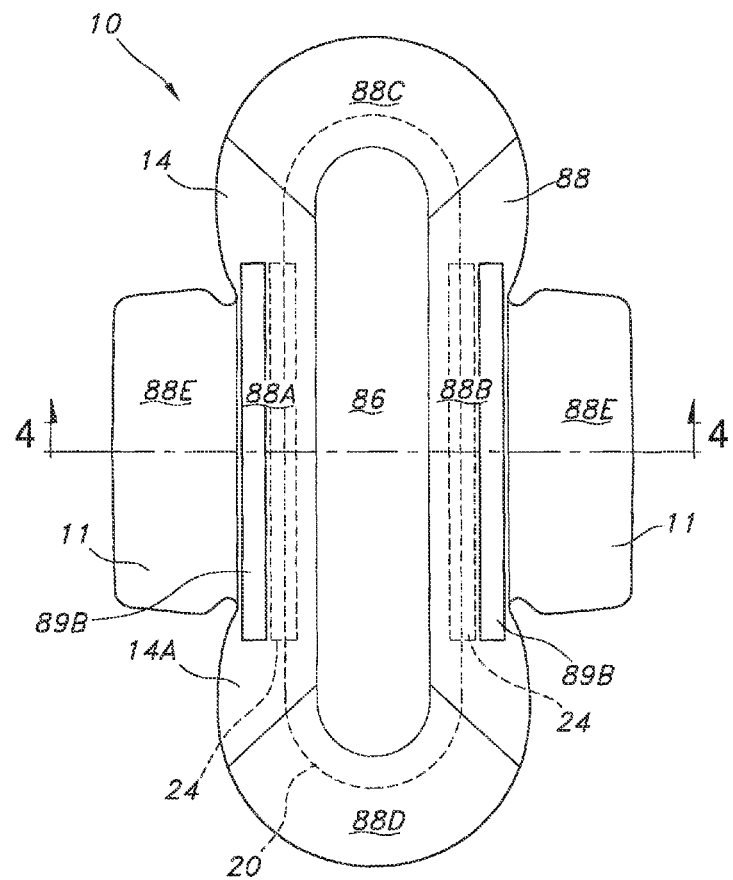
FIG. 3 is a top plan view of an alternative embodiment of a feminine hygienic pad of the invention illustrating the first and second regions of possible staining with body exudates.

Reference should now be made to FIG. 3 which is a top plan view of a feminine hygiene absorbent article 10 showing the user facing surface 14A of a topsheet layer 14. In this embodiment, the article 10 is also equipped with a pair of optional side wings 11 adapted to wrap around the crotch region of a wearer's/user's underwear (not shown). The topsheet layer 14 is composed of a first region 86 and a second region 88. The second region 88 can be formed from multiple sub-regions (88A, 88B, 88C, 88D and 88E). The first region 86 is generally centrally located as it is the primary location where the overall article 10 receives body exudates such as menses from the user of the product. While the first region 86 is shown as an elongated oval, it may be of any shape and generally will be of an irregular shape due to the nature of how the exudate is deposited onto the user facing surface 14A of the topsheet layer 14. The first region 86 can be drawn or defined in any shape but it is preferable that the first region be devoid of any decolorization means 89 along the longitudinal axis (L) and the transverse axis (T) and well as throughout the depth of the article 10 as defined by the vertical or depth axis (D). Thus the first region should be drawn so as to not encompass a decolorization means 89.

The second region 88 may completely surround the first region 86 in which case the second region will include sub-regions 88A, 88B, 88C and 88D. Thus, the second region 88 may completely surround the peripheral edge of the absorbent core 20 and preferably resides or is located outboard of the absorbent core peripheral edge. As with first region 86, second region 88 and any or all of its sub-regions (88A, 88B, 88C, 88D and 88E) may be of any shape, regular or irregular. The second region 88 may only surround a portion of the first region 86. For example, second region 88 may reside laterally outboard of first region 86 in which case second region 88 will include sub-regions 88A and 88B located in the lateral side portions of the article. Alternatively, second region 88 may reside longitudinally outboard of first region 86 in the longitudinal end portions of the article in which case second region 88 will include sub-regions 88C and 88D. Still further, second region 88 may be spaced apart from first region 86, as, for example, when second region 88 is formed from sub-regions 88E in the wings 11 of the article 10. The second region 88 may include the decolorization means 89 or the decolorization means 89 may be located between the first region 86 and the second region 88.

Figure 4:
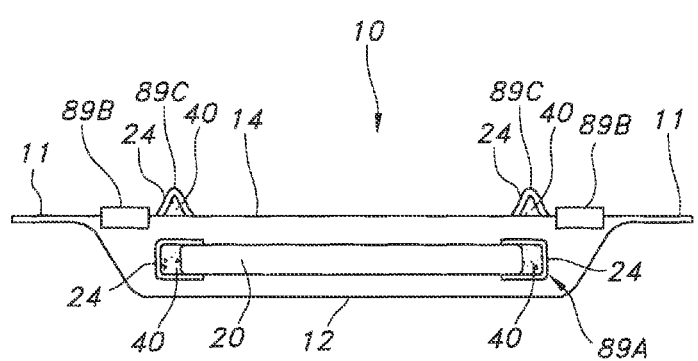
FIG. 4 is a cross-sectional side view of FIG. 3 taken along line 4-4.

Turning to FIG. 4, there is shown a cross-section of an article 10 with additional decolorization means 89C shown as compared to FIG. 3. In this embodiment, the article includes a topsheet layer 14, a backsheet layer 12 and an absorbent core 20 with a peripheral edge disposed between the topsheet layer 14 and the backsheet layer 12. The article 10 is also fitted with a pair of wings 11 adapted to wrap around the crotch region of a wearer's underwear (not shown). The article 10 is fitted with one or more decolorization means 89 which may be located within the interior of the article 10 such as in association with the absorbent core 20 as shown by element 89A or within or as a part of the topsheet layer 14 as shown by element 89B or on the user facing surface 14A of the topsheet layer 14 as shown by element (89C). When the decolorization means 89 is used in the vicinity of the peripheral edge of the absorbent core, not only is it desirable that the decolorization means extend beyond the peripheral edge of the absorbent core 20 but in certain embodiments it is desirable that the decolorization means 89A extend over a portion of the absorbent core 20. In this way, the size of the stain in the first region 86 will appear smaller than the size of the actual underlying stain. When the decolorization means 89 is used in conjunction with the topsheet layer 14 such as is shown by the decolorization means 89B, the decolorization means 89B can be a separate material or it can be a chemistry such as the aforementioned PEG which has been applied to a surface of or impregnated into the topsheet layer 14. Again, these locations are illustrative only and other designs and combinations are also within the scope of the present invention as illustrated by the previous drawings and their associated descriptions—see FIGS. 1 et al. and 2 et al. Further, while multiple decolorization means 89 are shown in FIGS. 4 and 5, only a single one may be necessary.

Figure 5:
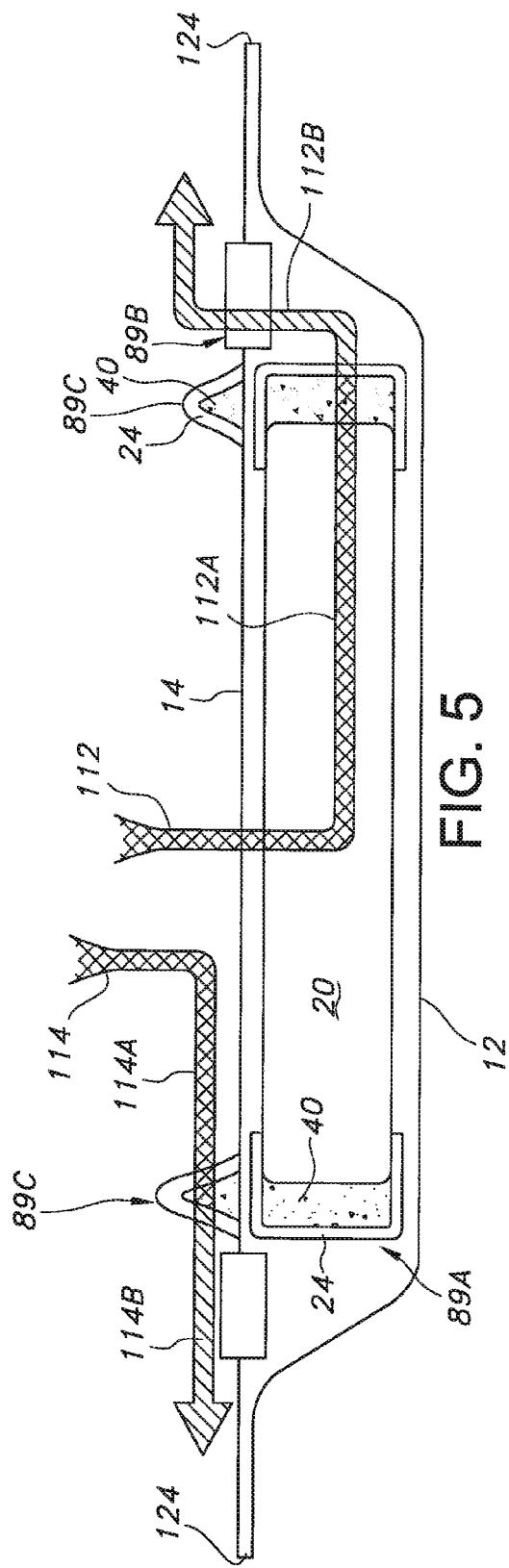
FIG. 5 is another cross-sectional side view of FIG. 3 taken along line 4-4.
Figure 6:
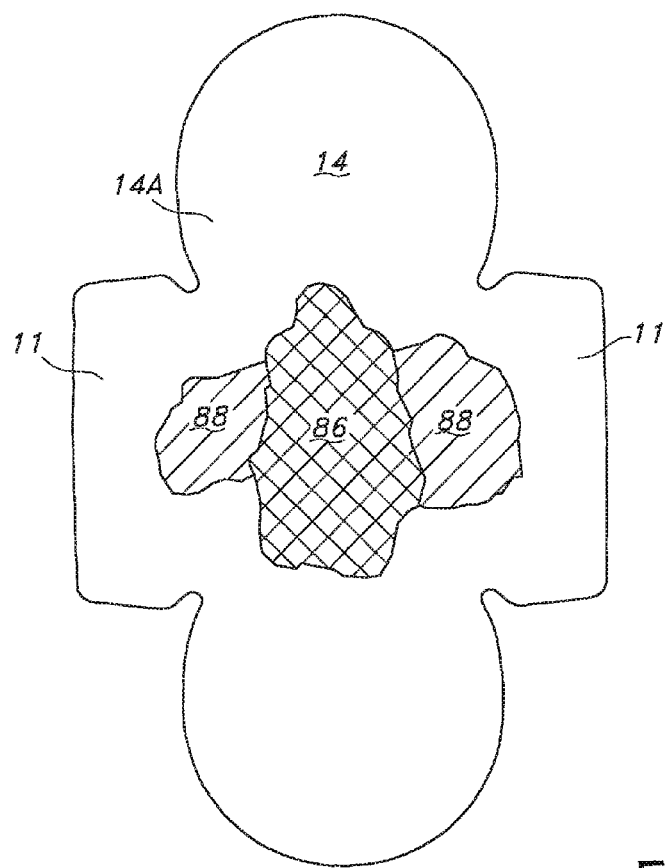
FIG. 6 is a top plan view of an alternative embodiment of a feminine hygienic pad of the invention illustrating the first and second regions of possible staining with body exudates.

In FIGS. 4 and 5, the decolorization means 89A is a wrap 24 of meltblown microfibers (MBMF) that overlaps the upper and lower surfaces and the side edges of the absorbent core 20 and the MBMF extends laterally outboard of the absorbent core 20. If desired, the MBMF may be treated with or contain PEG 40 or one of the other decolorizing chemical agents described herein. The decolorization means 89A may extend partially or entirely along the lateral side edges of the absorbent core 20 in the lateral side portions of the article. It may be located only in the longitudinal end portions of the overall article 10 and/or absorbent core 20 or it may extend completely around the entire periphery of the absorbent core 20. The decolorization means 89B may be located in or on a portion of the topsheet 14 in the form of an additional layer 24 or a chemical version 40 impregnated into a portion of the topsheet layer 14. Finally, the decolorization means 89C may be a dam-like structure associated with or integral to the user facing surface 14A of the topsheet layer 14 such as was previously described herein.

Turning to FIG. 5 there is shown the same cross-section as in FIG. 4 but this time with a series of arrows 112 and 114 which are meant to schematically illustrate the deposition of body exudate (in this case menstrual fluid) down onto and into the article 10. A first portion 112A and 114A respectively of arrows 112 and 114 are shown with cross-hatching (xxx) while a second portion 112B and 114B respectively of arrows 112 and 114 are shown with single slash marks (///). The first portion 112A and 114A is meant to represent menstrual fluid that has not been processed and passed through one of the decolorization means 89 while the second portion 112B and 114B of respective arrows 112 and 114 is meant to represent the same menstrual fluid after having been processed and passed through one or more of the decolorization means 89.

Menses or menstrual fluid is primarily made up of blood cells, endometrial tissue, vaginal epithelial cells and cervicovaginal secretions. Its composition will vary from individual to individual and will also vary depending on the point in the menstruation cycle during which the fluid is sampled. In this regard it is the hemoglobin within the red blood cells that is the easiest to track and measure. As described previously, the various forms of decolorization means disclosed herein have the ability to filter out some or all of those portions of the menses that give it its dark red color. As a result, once the menses has passed through the decolorization means 89, the remaining fluid emanating from the other side of the decolorization means 89 (as shown by the second portion 112B and 114B of arrows 112 and 114) is visually lighter in color as it has a lower content of one of more of the components including the red blood cells than the portion of the menses on the other side of the decolorization means 89 as represented by first portion 112A and 114A of arrows 112 and 114. Arrow 112 is shown flowing down through the topsheet layer 14 and into the absorbent core 20, out of one of the peripheral edges of the absorbent core 20 and then back up and out of the topsheet layer 14 to demonstrate a possible leak from the product. Though not shown, it could also flow out the bottom of the absorbent core 20 and if leakage was to occur, it could again flow out of the topsheet layer 14 or out one of the lateral or longitudinal edges 124 of the article 10 where the topsheet layer 14 and the backsheet layer 12 are joined to one another.

Following the flow path of the menses represented by arrow 112, the menses first enters the article 10 by way of the user facing surface 14A of topsheet layer 14. The insult of the menses takes place is the first region 86 as shown in FIG. 3 which is devoid of decolorization means 89. The flow of menses then travels down into the absorbent core 20 (optionally through one or more intermediate surge or transfer layers—not shown). As the menses continues to fill the absorbent core 20, it may come in contact with the decolorization means 89C where the darker components, such as the red blood cells of the menses will be physically trapped and retained or chemically altered as to its color. Consequently, the remaining portion of the menstrual fluid which passes through the decolorization means 89C will have a lighter color as observed visually by the human eye. In addition, portions of the menstrual fluid-containing components can be physically extracted from the article 10 and analyzed as to the quantities of red blood cells and it can be seen that the portion of the fluid on the outboard side of the decolorization means 89C (as represented by the second portion 112B of arrow 112) will have a lower concentration of red blood cells than on the inboard side (as represented by the first portion 112A of arrow 112). The lighter color menses is meant to represent and be identified as the second region 88 relative to FIG. 3.

Continuing to follow the path of arrow 112 it can be seen that if the capacity of the article 10 is sufficiently tested, the lighter-colored menstrual fluid may actually flow back towards the topsheet layer 14 (this is commonly referred to as "rewet") and exit the topsheet layer 14 by passing through the optional decolorization means 89B which can provide further decolorization of the menstrual fluid before it exists the product. By subjecting this menstrual fluid to this decolorization process, the likelihood of the exiting fluid causing significant staining of the wearer's clothing is greatly reduced. This in turn means the user of the product can feel more confident when wearing such a product fitted with the aforementioned decolorization means 89.

While it is desired that most of the menstrual flow insulting the article 10 flows down into the absorbent core 20 via the topsheet layer 14, it is not uncommon for there to be "gushes" of fluid that are not able to be quickly absorbed by the article 10. Due to the smaller size as well as the narrow and thin construction of feminine hygiene products today and the fact that the menses is typically deposited onto the most narrow portion of the article, the crotch portion, some of the menstrual fluid may start to run laterally or longitudinally off the sides of the product. Typically this path is off the lateral sides of the product and this flow path is represented by arrow 114. Once again, because of the positioning of the decolorization means 89A, the menses as it passes across the user facing side 14A of the topsheet layer 14 will come in contact with the decolorization means 89A which will serve to trap or decolor the red blood cell component of the menses thus rendering the fluid emanating from the outboard side of the decolorization means 89A (represented by the second portion 114 of arrow 114) lighter in color with a lower concentration of the red blood cells and thus this fluid will be less likely to stain the clothing of the wearer. In addition, if the topsheet layer 14 is fitted with an additional decolorization means 89B, further decolorization of the menses may take place before it exits the product. The visual effect of this decolorization process is shown schematically in FIG. 6.

Given the length of time such feminine hygiene products can be worn, it is not uncommon for the wearer to do periodic checks of the product to determine if it is time to change the product. As the wearer lowers the undergarment to which the product is attached, the user facing surface 14A will be visually inspected. Due to the porous nature of the topsheet layer 14, it is often possible for the wearer to be able to see not only the menses that is residing in and/or on top of and staining the topsheet layer 14 but it is also sometimes possible to see some portion of the menses that is contained in one or more of the lower layers below the topsheet layer 14. The initial insult area of the deposited menses will typically appear as the stain on the topsheet layer 14 represented by the first region 86. See FIG. 6. If menstrual fluid has flowed across the topsheet layer 14 as represented by arrow 114 in FIG. 5, and has been processed by one of the decolorization means 89, it will be represented by the second region 88 in FIG. 6. The same can be true if the fluid has followed the path of arrow 112. In addition, even if the fluid that has been processed by the decolorization means 89 has not rewet the topsheet layer 14, it still may be possible to view this lighter colored fluid which contains less red blood cells than the fluid in the first region 86 through the topsheet layer 14 in the second region 88. In either event, the fact that the fluid contained in the second region 88 is lighter in color can act to reassure the wearer that the product is working adequately. This is especially true as lateral flow is not an indication that the entire capacity of the feminine hygiene product has been utilized as it is often the case that there is much more reserve capacity due to the complete vertical depth and longitudinal length of the absorbent core having not been fully utilized.

Figure 7:
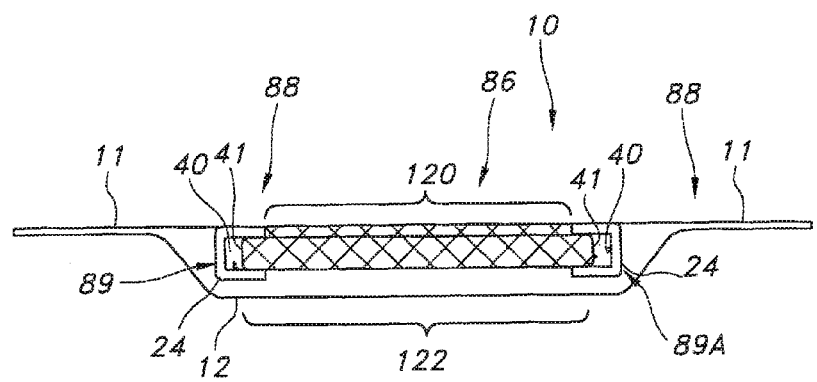
FIG. 7 is a cross-sectional view of a feminine hygiene pad of the invention illustrating the reduction in stain size of the deposited exudate on the top portion of the product as compared to the lower portion of the product.

Another advantage of the feminine hygiene products disclosed herein is the manner in which the vertical filling of the article will appear as a result of the use of the decolorization means 89. Turning to FIG. 7, there is shown another cross-section of an article 10 according to the present invention. In this embodiment, the peripheral edge (in this case the lateral side edges 41 of the absorbent core 20) is fitted with a decolorization means 89 which is the same as that described with respect to FIG. 10 of the drawings. In this embodiment, a feminine hygiene absorbent personal care article 10 comprises a topsheet layer 14, a backsheet layer 12, at least one absorbent core layer 20 positioned between the topsheet layer 14 and the backsheet layer 12 and a decolorizing means 89 associated with the article 10 (in this case the decolorization means 89 extends outboard of the peripheral edge, specifically the side edge, of the absorbent core 20). The decolorization means 89 includes a wrapping layer 24 of MBMF wrapping the edges 41 of the absorbent core 20 and further encapsulating a quantity of PEG 40 between the edges 41 of the core and the wrapping layer 24. As with the other embodiments, the topsheet layer 14 has a body side or user facing surface 14A having a first region 86 for receiving said body exudate. The body exudate in the first region creates a first stain region on the topsheet layer 14 designated by the "X's" in bracket 120 with a lateral dimension and a longitudinal dimension that defines a first size. Because the wrapping layer 24 and the PEG 40 encapsulate the edges of the absorbent core 20 the area above (second region 88) this portion of the absorbent core will either not show any staining or the staining will be lighter in color. As a result, the article 10 will have a second stain region designated by the "X's" in bracket 122 located below the first stain region 120 relative to the depth axis D. The second stain region 122 will have a lateral dimension and a longitudinal dimension that defines a second size and the second size will be larger than the first size. This is due, at least in part, to the decolorization means 89A and specifically the wrapping layer 24 overlapping a portion of the top surface of the absorbent core 20 in the vicinity of the peripheral edge of the absorbent core 20. Thus, when the wearer observes the in situ product from above, the stain in the first stain region will actually appear smaller that the lower second stain region.

Menses or menstrual fluid is primarily made up of blood cells, endometrial tissue, vaginal epithelial cells and cervico-vaginal secretions. Its composition will vary from individual to individual and will also vary depending on the point in the menstruation cycle during which the fluid is sampled. The primary function of the decolorization means described herein is to filter or trap some of the heavier components of the menstrual fluid including the red blood cells as this is one of the primary contributors to the visual staining of the product and the clothing of the wearer of the product. Desirably, the red blood cells are confined within certain regions of the product which reduce such staining and which thus sends more positive signals to the wearer regarding the efficiency and protection provided by the product. In this regard it is the hemoglobin within the red blood cells that is the easiest to track and measure.

As mentioned above, if the product is performing properly, the red staining will be relegated to a first region 86 of the product and the outboard regions (second regions 88) will have a lighter color or appearance when viewed with the naked eye. Normally, this difference in color can be viewed by the human eye when the product is held in the range of 6 to 24 inches from the eye (15 to 61 centimeters). In addition to visual inspection for this attribute of the product, testing can also be performed to quantify this alteration in the visual appearance and the change in the physical characteristics of the body exudate (menses) in the second region 88 as compared to the first region 86. See, for example, US 2003/0114818 to Benecke et al. which is incorporated herein by reference in its entirety. In this reference there is disclosed a test for measuring the change in the visual perception of the menses contained in an absorbent article. This change is referred to in this reference as the "delta E" and a method for determining this delta E is set forth therein. As a result, a delta E can be measured for the first region 86 and a separate delta E can be measured for the second region 88. For purposes of the present invention, the delta between the delta E for the first region 86 and the delta E for the second region should be greater than or equal to twenty (20), alternatively greater than or equal to forty (40), alternatively greater than or equal to sixty (60), alternatively greater than or equal to eighty (80). That is, for example, the delta E for the first region 86 should be at least twenty points higher than the delta E of the second region 88 where some or all of the red blood cells in the menstrual fluid have been removed by way of the decolorization means 89. For purposes of this test, if bench scale testing is being done versus using actual used product, the menses simulant referenced herein (U.S. Pat. No. 5,883,231 and the publication by D, Guralski, Candee Krautkramer, Brian Lin, Jack Lindon, Teuta Elshani, Aneshia Ridenhour, entitled "A Biological Menses Simulant Using a "Batch" Homogenization Process", and published as Document IPCOM000198395D at ip.com, 6 Aug. 2010) should be used in place of the canine blood formulation described in US 2003/0114818. Also note that if any masking layers are being used in an area for testing that such masking layers should be removed prior to performing the test.

In addition to there being a visual difference in the color of the staining in one region versus another, the decolorization means as described above can also alter the physical characteristics of the menses in the second region 88 and compared to the first region 86. As mentioned above, this is due, at least in part, to the removal of some or all of the red blood cells from the menses in the second region 88. The fact that this has happened can be measured by measuring the hemoglobin level in the fluid in the first region 86 and comparing it to the second region 88. The second region 88 should have less hemoglobin and thus fewer red blood cells as compared to the first region 86. In addition, it is likely that the decolorization means 89 will have a higher level of hemoglobin and thus red blood cells than the second region 88 and most likely a higher level than the first region 86. The amount of hemoglobin in samples of stained material in the first region 86, the second region 88 and the decolorization means 89 can be determined by any number of test methods familiar to those who perform blood testing and analysis. See, for example, U.S. Pat. No. 4,773,423 to Hakky which is incorporated herein by reference in its entirety as a reference for such test methods.

While the invention has been described in detail with respect to the specific embodiments thereof, it will be appreciated that those skilled in the art, upon attaining an understanding of the foregoing, may readily conceive of alterations to, variations of, and equivalents to these embodiments. For example, while menses has been the primary body exudate used for the examples, the present invention may also be used for other body exudates including blood, feces and urine. Accordingly, the scope of the present invention should be assessed as that of the appended claims and any equivalent thereto.

We claim:

1. A personal care absorbent article for receiving a body exudate comprising a topsheet layer, a backsheet layer, and at least one absorbent core layer having a peripheral edge positioned between said topsheet layer and said backsheet layer, said article defining a longitudinal axis, a transverse axis and a vertical axis, said topsheet layer having a user facing surface having a first region for receiving said body exudate comprising menses including red blood cells, said user facing surface having a second region capable of receiving said body exudate from said first region and a decolorization material capable of filtering said red blood cells within said body exudate, said decolorization material altering the visual appearance of said body exudate in said second region as compared to said first region by lowering the content of said red blood cells in said second region as compared to said first region as said body exudate travels from said first region to said second region through said decolorization material, wherein said decolorization material comprises a wrapping layer which wraps at least a portion of said peripheral edge of said absorbent core layer and extends across at least a portion of a user facing surface of said absorbent core layer.

2. The personal care absorbent article of claim 1 wherein said decolorization material comprises a meltblown microfiber material.

3. The personal care absorbent article of claim 2 wherein said body exudate in said first region is of a darker color than said second region due to said first region having a higher content of red blood cells than said second region.

4. The personal care absorbent article of claim 1 wherein said second region completely surrounds said first region.

5. The personal care absorbent article of claim 1 wherein said second region is positioned laterally outboard of said first region.

6. The personal care absorbent article of claim 1 wherein said article has opposed longitudinal end portions and said second region is located in said opposed longitudinal end portions of said article.

7. The personal care absorbent article of claim 1 wherein said article has opposed lateral side portions and said second region is located in said opposed lateral side portions of said article.

8. The personal care absorbent article of claim 1 which further includes wings associated with said article adapted to wrap around the crotch region of a wearer's underwear, said second region extending into said wings.

9. A personal care absorbent article for receiving a body exudate comprising a topsheet layer, a backsheet layer, and at least one absorbent core layer having a peripheral edge positioned between said topsheet layer and said backsheet layer, said article defining a longitudinal axis, a transverse axis and a vertical axis, said topsheet layer having a user facing surface having a first region for receiving said body exudate comprising menses including red blood cells, said user facing surface having a second region capable of receiving said body exudate from said first region and a decolorization material capable of filtering said red blood cells within said body exudate, said decolorization material altering the visual appearance of said body exudate in said second region as compared to said first region by lowering the content of said red blood cells in said second region as compared to said first region as said body exudate travels from said first region to said second region through said decolorization material, wherein said decolorization material is associated with said topsheet layer and forms a dam-like structure extending above said user facing surface of said topsheet layer.

10. The personal care absorbent article of claim 9 wherein said decolorization material comprises a meltblown microfiber layer.

11. The personal care absorbent article of claim 10 wherein said decolorization material has a higher concentration of said red blood cells than either said first region or said second region.

12. The personal care absorbent article of claim 9 wherein said second region completely surrounds said first region.

13. The personal care absorbent article of claim 9 wherein said second region is positioned laterally outboard of said first region.

14. The personal care absorbent article of claim 9 wherein said article has opposed longitudinal end portions and said second region is located in said opposed longitudinal end portions of said article.

15. The personal care absorbent article of claim 9 wherein said article has opposed lateral side portions and said second region is located in said opposed lateral side portions of said article.

16. The personal care absorbent article of claim 9 which further includes wings associated with said article adapted to wrap around the crotch region of a wearer's underwear, said second region extending into said wings.

* * * * *